(12) United States Patent
Albert et al.

(10) Patent No.: US 7,348,028 B2
(45) Date of Patent: Mar. 25, 2008

(54) CHRONOTHERAPEUTIC DILTIAZEM FORMULATIONS AND THE ADMINISTRATION THEREOF

(76) Inventors: Kenneth Stephen Albert, 87 Greenwood La., Mt. Kisco, NY (US) 10549-4045; Theophilus Jones Gana, 1504 Shields Ter., Leesburg, VA (US) 20176-6620; Paul Maes, 10205 Windsor View Dr., Potomac, MD (US) 20854-4020

( * ) Notice: Subject to any disclaimer, the term of this patent is extended or adjusted under 35 U.S.C. 154(b) by 538 days.

(21) Appl. No.: 10/657,752

(22) Filed: Sep. 9, 2003

(65) Prior Publication Data

US 2004/0176352 A1    Sep. 9, 2004

Related U.S. Application Data

(60) Provisional application No. 60/408,872, filed on Sep. 9, 2002.

(51) Int. Cl.
| | |
|---|---|
| *A61K 9/14* | (2006.01) |
| *A61K 9/16* | (2006.01) |
| *A61K 9/20* | (2006.01) |
| *A61K 9/22* | (2006.01) |

(52) U.S. Cl. .................. 424/489; 424/490; 424/464; 424/468

(58) Field of Classification Search ............ 424/489, 424/451, 464
See application file for complete search history.

(56) References Cited

U.S. PATENT DOCUMENTS

| 4,721,619 | A | | 1/1988 | Panoz et al. |
|---|---|---|---|---|
| 4,960,596 | A | | 10/1990 | Debregeas et al. |
| 5,229,135 | A | * | 7/1993 | Philippon et al. |
| 5,288,505 | A | | 2/1994 | Deboeck et al. |
| 5,344,657 | A | * | 9/1994 | Desmolin |
| 5,529,790 | A | | 6/1996 | Eichel et al. |
| 5,616,345 | A | | 4/1997 | Geoghegan et al. |
| 6,524,620 | B2 | * | 2/2003 | Chen et al. |
| 7,108,866 | B1 | | 9/2006 | Albert et al. |

FOREIGN PATENT DOCUMENTS

WO    WO 01/41744    6/2001

* cited by examiner

*Primary Examiner*—Humera N Sheikh
(74) *Attorney, Agent, or Firm*—Oblon, Spivak, McClelland, Maier & Neustadt, P.C.

(57) ABSTRACT

A method of treating or preventing myocardial ischemia in a patient in need thereof comprising administration of a controlled-release Galenical preparation of pharmaceutically acceptable Diltiazem including the pharmaceutically acceptable salts thereof, suitable for evening dosing every 24 hours containing from about 180 mg to about 420 mg of the form of Diltiazem associated with excipients to provide controlled (sustained) release of the form of Diltiazem for providing a $C_{max}$ of Diltiazem in the blood at between about 10 hours and about 17 hours after administration, the preparation comprising the form of Diltiazem in oral sustained-release dosage form in which the Diltiazem is adapted to be released after administration over a prolonged period of time and exhibits when given to humans
(i) a higher bioavailability when given at night compared to when given in the morning without food according to FDA guidelines or criteria and
(ii) bioequivalence when given in the morning with and without food according to the same FDA guidelines or criteria.

75 Claims, 18 Drawing Sheets

Diltiazem AUCt PK Summary

Formulation According to Embodiment of Invention

Figure 1:
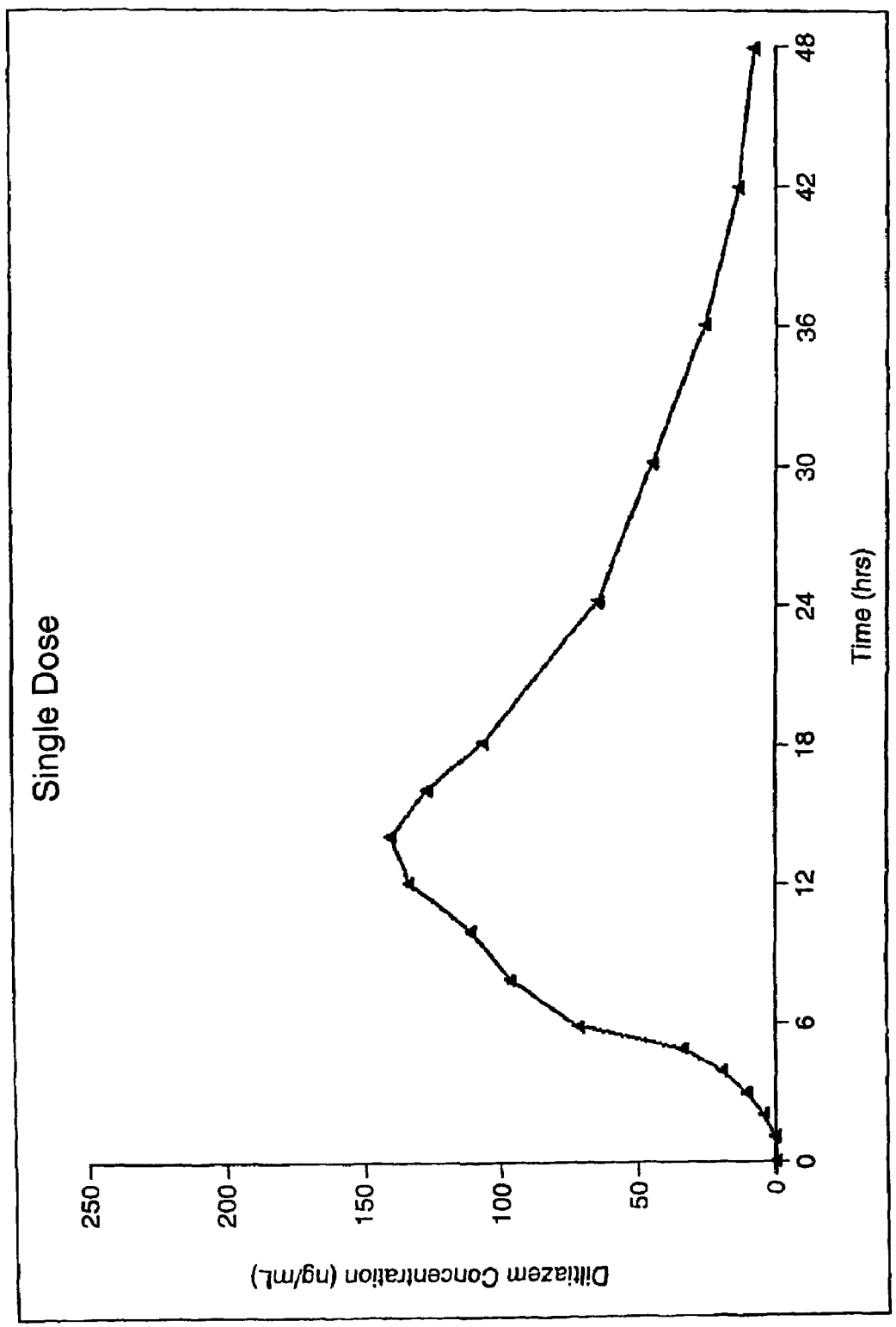

| Subject | Morning Fasting AUCt | Log AUCt | Morning Fed AUCt | Log AUCt | Night Dosing AUCt | Log AUCt | Morning Fed/Fast Ratio | Night/Morning Ratio |
|---|---|---|---|---|---|---|---|---|
| 2 | 1730.75 | 7.46 | 2647.15 | 7.88 | 1987.11 | 7.59 | 1.53 | 1.15 |
| 3 | 2712.98 | 7.91 | 2336.67 | 7.76 | 3249.94 | 8.09 | 0.86 | 1.20 |
| 4 | 2688.34 | 7.90 | 1907.61 | 7.55 | 2892.21 | 7.97 | 0.71 | 1.08 |
| 5 | 4192.37 | 8.34 | 4108.65 | 8.32 | 4702.33 | 8.46 | 0.98 | 1.12 |
| 6 | 3074.51 | 8.03 | 2887.98 | 7.97 | 3900.06 | 8.27 | 0.94 | 1.27 |
| 7 | 1629.81 | 7.40 | 1847.56 | 7.52 | 2723.36 | 7.91 | 1.13 | 1.67 |
| 8 | 941.10 | 6.85 | 1970.97 | 7.59 | 1835.11 | 7.51 | 2.09 | 1.95 |
| 9 | 3144.13 | 8.05 | 3462.59 | 8.15 | 2923.86 | 7.98 | 1.10 | 0.83 |
| 10 | 2074.94 | 7.64 | 2997.45 | 8.01 | 4028.83 | 8.30 | 1.44 | 1.94 |
| 11 | 3653.96 | 8.20 | 2771.53 | 7.93 | 3464.72 | 8.15 | 0.76 | 0.95 |
| 12 | 2684.22 | 7.90 | 3790.43 | 8.24 | 3141.47 | 8.05 | 1.41 | 1.17 |
| 13 | 3352.69 | 8.12 | 3751.95 | 8.23 | 3708.83 | 8.22 | 1.12 | 1.11 |
| 14 | 2988.61 | 8.00 | 3665.60 | 8.21 | 3141.05 | 8.05 | 1.23 | 1.05 |
| 15 | 6796.97 | 8.82 | 8204.22 | 9.01 | 7578.33 | 8.93 | 1.21 | 1.11 |
| 16 | 2873.70 | 7.96 | 4644.79 | 8.44 | 4192.09 | 8.34 | 1.62 | 1.46 |
| 17 | 4468.33 | 8.40 | 4222.55 | 8.35 | 3762.50 | 8.23 | 0.94 | 0.84 |
| 18 | 5654.29 | 8.64 | 5635.72 | 8.64 | 7159.38 | 8.88 | 1.00 | 1.27 |
| 19 | 4944.07 | 8.51 | 5107.44 | 8.54 | 4812.20 | 8.48 | 1.03 | 0.97 |
| 20 | 2986.73 | 8.00 | 2988.34 | 8.00 | 2791.23 | 7.93 | 1.00 | 0.93 |
| 21 | 2908.88 | 7.98 | 3314.12 | 8.11 | 4389.98 | 8.39 | 1.14 | 1.51 |
| 22 | 4270.43 | 8.36 | 3790.06 | 8.24 | 3631.01 | 8.20 | 0.89 | 0.85 |
| 23 | 6150.18 | 8.72 | 6092.56 | 8.71 | 7478.22 | 8.92 | 0.99 | 1.22 |
| 25 | 2926.46 | 7.98 | 5633.64 | 8.64 | 4839.10 | 8.48 | 1.93 | 1.65 |
| 26 | 3928.61 | 8.28 | 4614.43 | 8.44 | 4359.77 | 8.38 | 1.17 | 1.11 |
| 27 | 3637.94 | 8.20 | 4587.48 | 8.43 | 4063.15 | 8.31 | 1.26 | 1.12 |
| 28 | 4177.76 | 8.34 | 4945.31 | 8.51 | 6689.14 | 8.81 | 1.18 | 1.60 |
| 29 | 3609.69 | 8.19 | 2720.67 | 7.91 | 2163.20 | 7.68 | 0.75 | 0.60 |
| 30 | 4483.17 | 8.41 | 5222.54 | 8.56 | 5587.50 | 8.63 | 1.16 | 1.25 |
| 32 | 4058.04 | 8.31 | 3531.47 | 8.17 | 3082.67 | 8.03 | 0.87 | 0.76 |
| Mean | 3542.88 | 8.10 | 3910.40 | 8.21 | 4078.57 | 8.25 | 1.15 | 1.20 |
| SD | 1304.23 | 0.41 | 1431.24 | 0.36 | 1554.69 | 0.37 | 0.33 | 0.33 |
| CV | 36.81 | 5.08 | 36.60 | 4.43 | 38.12 | 4.46 | 28.23 | 27.33 |
| Median | 3352.69 | 8.12 | 3751.95 | 8.23 | 3762.50 | 8.23 | 1.12 | 1.12 |
| Geo Mean | 3292.83 | 8.09 | 3671.24 | 8.20 | 3818.30 | 8.24 | 1.11 | 1.16 |

Fed/Fasting Ratio (Morning Dosing)

| | | |
|---|---|---|
| Ratio of Means | 1.10 | # |
| Ratio of Geo Means | 1.11 | # |
| Avg of Individual Ratios | 1.15 | # |

Night/Morning Ratio

| | |
|---|---|
| Ratio of Means | 1.15 |
| Ratio of Geo Means | 1.16 |
| Avg of Individual Ratios | 1.20 |

Fig. 9A

Diltiazem Cmax PK Summary

Formulation According to Embodiment of Invention

| Subject | Morning Fasting Tmax | Morning Fasting Cmax | Morning Fasting Log Cmax | Morning Fed Tmax | Morning Fed Cmax | Morning Fed Log Cmax | Night Dosing Tmax | Night Dosing Cmax | Night Dosing Log Cmax | Morning Fed/Fast Ratio | Night/Morning Ratio |
|---|---|---|---|---|---|---|---|---|---|---|---|
| 2 | 10.0 | 98.63 | 4.59 | 10.0 | 187.71 | 5.23 | 13.0 | 143.84 | 4.97 | 1.90 | 1.46 |
| 3 | 13.0 | 136.18 | 4.91 | 11.0 | 123.04 | 4.81 | 10.0 | 246.57 | 5.51 | 0.90 | 1.81 |
| 4 | 15.0 | 133.23 | 4.89 | 10.0 | 118.68 | 4.78 | 10.0 | 191.44 | 5.25 | 0.89 | 1.44 |
| 5 | 8.0 | 222.52 | 5.41 | 8.0 | 195.66 | 5.28 | 12.0 | 254.96 | 5.54 | 0.88 | 1.15 |
| 6 | 12.0 | 150.85 | 5.02 | 8.0 | 164.11 | 5.10 | 16.0 | 179.67 | 5.19 | 1.09 | 1.19 |
| 7 | 10.0 | 90.58 | 4.51 | 14.0 | 121.64 | 4.80 | 12.0 | 179.87 | 5.19 | 1.34 | 1.98 |
| 8 | 8.0 | 65.68 | 4.18 | 11.0 | 119.30 | 4.78 | 11.0 | 133.35 | 4.89 | 1.82 | 2.03 |
| 9 | 13.0 | 155.46 | 5.05 | 6.0 | 292.70 | 5.68 | 12.0 | 175.62 | 5.17 | 1.88 | 1.13 |
| 10 | 8.0 | 95.45 | 4.56 | 6.0 | 166.91 | 5.12 | 13.0 | 196.94 | 5.28 | 1.75 | 2.08 |
| 11 | 14.0 | 212.41 | 5.36 | 11.0 | 154.64 | 5.04 | 14.0 | 183.66 | 5.21 | 0.73 | 0.86 |
| 12 | 10.0 | 117.75 | 4.77 | 10.0 | 201.43 | 5.31 | 11.0 | 174.95 | 5.16 | 1.71 | 1.49 |
| 13 | 14.0 | 149.90 | 5.01 | 13.0 | 188.51 | 5.24 | 10.0 | 208.78 | 5.34 | 1.26 | 1.39 |
| 14 | 13.0 | 139.54 | 4.94 | 6.0 | 205.35 | 5.32 | 13.0 | 187.32 | 5.23 | 1.47 | 1.34 |
| 15 | 16.0 | 266.48 | 5.59 | 15.0 | 330.83 | 5.80 | 13.0 | 450.34 | 6.11 | 1.24 | 1.69 |
| 16 | 13.0 | 134.55 | 4.90 | 8.0 | 281.74 | 5.64 | 10.0 | 236.10 | 5.46 | 2.09 | 1.75 |
| 17 | 12.0 | 224.65 | 5.41 | 10.0 | 244.82 | 5.50 | 10.0 | 203.51 | 5.32 | 1.09 | 0.91 |
| 18 | 14.0 | 281.88 | 5.64 | 10.0 | 308.25 | 5.73 | 14.0 | 479.11 | 6.17 | 1.09 | 1.70 |
| 19 | 15.0 | 227.89 | 5.43 | 11.0 | 262.82 | 5.57 | 13.0 | 231.49 | 5.44 | 1.15 | 1.02 |
| 20 | 14.0 | 137.54 | 4.92 | 10.0 | 175.76 | 5.17 | 10.0 | 173.93 | 5.16 | 1.28 | 1.26 |
| 21 | 13.0 | 164.75 | 5.10 | 13.0 | 197.63 | 5.29 | 13.0 | 301.72 | 5.71 | 1.20 | 1.83 |
| 22 | 16.0 | 182.52 | 5.21 | 11.0 | 207.19 | 5.33 | 10.0 | 247.06 | 5.51 | 1.14 | 1.35 |
| 23 | 18.0 | 269.97 | 5.60 | 10.0 | 340.21 | 5.83 | 13.0 | 500.82 | 6.22 | 1.26 | 1.86 |
| 25 | 10.0 | 166.06 | 5.11 | 8.0 | 322.55 | 5.78 | 10.0 | 263.27 | 5.57 | 1.94 | 1.59 |
| 26 | 13.0 | 208.19 | 5.34 | 10.0 | 237.50 | 5.47 | 10.0 | 235.12 | 5.46 | 1.14 | 1.13 |
| 27 | 10.0 | 162.47 | 5.09 | 8.0 | 255.85 | 5.54 | 11.0 | 170.18 | 5.14 | 1.57 | 1.05 |
| 28 | 13.0 | 218.59 | 5.39 | 11.0 | 236.10 | 5.46 | 11.0 | 384.02 | 5.95 | 1.08 | 1.76 |
| 29 | 13.0 | 215.15 | 5.37 | 13.0 | 160.73 | 5.08 | 12.0 | 129.94 | 4.87 | 0.75 | 0.60 |
| 30 | 14.0 | 242.88 | 5.49 | 12.0 | 244.58 | 5.50 | 10.0 | 336.64 | 5.82 | 1.01 | 1.39 |
| 32 | 12.0 | 303.43 | 5.72 | 15.0 | 204.09 | 5.32 | 11.0 | 231.33 | 5.44 | 0.67 | 0.76 |
| Mean | 12.6 | 178.45 | 5.12 | 10.2 | 215.53 | 5.33 | 11.6 | 242.46 | 5.42 | 1.29 | 1.41 |
| SD | 2.5 | 61.85 | 0.37 | 2.5 | 64.85 | 0.31 | 1.6 | 98.98 | 0.36 | 0.40 | 0.39 |
| CV | 19.8 | 34.66 | 7.32 | 24.3 | 30.09 | 5.83 | 14.1 | 40.82 | 6.58 | 30.89 | 27.83 |
| Median | 13.0 | 164.75 | 5.10 | 10.0 | 204.09 | 5.32 | 11.0 | 208.76 | 5.34 | 1.20 | 1.39 |
| Geo Mean | 12.3 | 167.47 | 5.11 | 9.9 | 206.00 | 5.32 | 11.5 | 228.83 | 5.41 | 1.23 | 1.35 |

Fed/Fasting Ratio (Morning Dosing)

Ratio of Means 1.21
Ratio of Geo Means 1.23
Avg of Individual Ratios 1.29

Night/Morning Ratio

Ratio of Means 1.36
Ratio of Geo Means 1.35
Avg of Individual Ratios 1.41

Fig. 9B

PK Summary (N=30)

Diltiazem PK

Open Capsule Sprinkled on Applesauce / Capsule Intact

| AUCt | | Cmax | |
|---|---|---|---|
| Ratio of Means % | 94.16 | Ratio of Means % | 93.35 |
| Ratio of Geo Means % | 93.98 | Ratio of Geo Means % | 93.00 |
| Avg of Individual Ratios % | 96.03 | Avg of Individual Ratios % | 95.73 |
| 90% C.I. | 88%-99% | 90% C.I. | 86%-99% |
| Intra-CV | 13.47% | Intra-CV | 16.07% |

Tmax

| | Mean |
|---|---|
| Open Capsule Sprinkled on Applesauce | 13.7 hours |
| Capsules Intact | 13.5 hours |

Fig. 10A

Diltiazem AUCt Results

Formulation According to Embodiment of Invention

| Subject | Open Capsules Sprinkled on Applesauce (A) | | Capsule Intact (B) | | (A:B) Ratio |
|---|---|---|---|---|---|
| | AUCt | Log Cmax | AUCt | Log Cmax | |
| 1 | 3937.18 | 8.28 | 3251.62 | 8.09 | 1.21 |
| 2 | 3792.89 | 8.24 | 5502.18 | 8.61 | 0.69 |
| 3 | 1616.35 | 7.39 | 2358.22 | 7.77 | 0.69 |
| 4 | 8209.44 | 9.01 | 7954.29 | 8.98 | 1.03 |
| 5 | 2171.26 | 7.68 | 2452.78 | 7.80 | 0.89 |
| 6 | 5710.90 | 8.65 | 7082.30 | 8.87 | 0.81 |
| 7 | 1983.56 | 7.59 | 2624.03 | 7.87 | 0.76 |
| 8 | 3862.46 | 8.26 | 3114.53 | 8.04 | 1.24 |
| 9 | 6069.65 | 8.71 | 4585.60 | 8.43 | 1.32 |
| 10 | 3907.33 | 8.27 | 6393.14 | 8.76 | 0.61 |
| 11 | 3842.58 | 8.25 | 4292.30 | 8.36 | 0.90 |
| 12 | 4873.82 | 8.49 | 6493.87 | 8.78 | 0.75 |
| 13 | 2707.85 | 7.90 | 3922.90 | 8.27 | 0.69 |
| 14 | 2553.27 | 7.85 | 2159.88 | 7.68 | 1.18 |
| 15 | 2042.47 | 7.62 | 2902.70 | 7.97 | 0.70 |
| 16 | 4650.14 | 8.44 | 4769.32 | 8.47 | 0.98 |
| 17 | 3705.72 | 8.22 | 3464.89 | 8.15 | 1.07 |
| 19 | 7861.69 | 8.97 | 6851.45 | 8.83 | 1.15 |
| 21 | 6151.00 | 8.72 | 6292.65 | 8.75 | 0.98 |
| 22 | 2138.64 | 7.67 | 1933.52 | 7.57 | 1.11 |
| 23 | 3983.50 | 8.29 | 5177.74 | 8.55 | 0.77 |
| 24 | 3939.51 | 8.28 | 3517.56 | 8.17 | 1.12 |
| 25 | 2318.36 | 7.75 | 2016.26 | 7.61 | 1.15 |
| 27 | 2061.09 | 7.63 | 1928.02 | 7.56 | 1.07 |
| 28 | 2871.31 | 7.96 | 3312.87 | 8.11 | 0.87 |
| 29 | 4305.14 | 8.37 | 3559.57 | 8.18 | 1.21 |
| 30 | 3190.17 | 8.07 | 3565.88 | 8.18 | 0.89 |
| 31 | 3422.16 | 8.14 | 3012.17 | 8.01 | 1.14 |
| 33 | 4906.47 | 8.50 | 5206.52 | 8.56 | 0.94 |
| 34 | 2969.19 | 8.00 | 3255.28 | 8.09 | 0.91 |
| Mean | 3859.17 | 8.17 | 4098.47 | 8.24 | 0.96 |
| SD | 1664.90 | 0.42 | 1708.24 | 0.41 | 0.20 |
| CV | 43.14 | 5.10 | 41.68 | 5.03 | 20.69 |
| Median | 3817.74 | 8.25 | 3538.57 | 8.17 | 0.96 |
| Geo Mean | 3546.16 | 8.16 | 3773.43 | 8.23 | 0.94 |

Test/Ref Ratio
Ratio of Means %    94.16
Ratio of Geo Means %    93.98
Avg of Individual Ratios    0.96
90% C.I.    88%-99%
Intra-CV    13.47%

Fig. 10B

Diltiazem Cmax Results

Formulation According to Embodiment of Invention

| Subject | Open Capsule Sprinkled on Applesauce (A) | | | Capsule Intact (B) | | | (A:B) Ratio |
|---|---|---|---|---|---|---|---|
| | Tmax | Cmax | Log Cmax | Tmax | Cmax | Log Cmax | |
| 1 | 13.0 | 184.35 | 5.22 | 13.0 | 228.99 | 5.43 | 0.81 |
| 2 | 14.0 | 192.44 | 5.26 | 12.0 | 286.72 | 5.66 | 0.67 |
| 3 | 13.0 | 103.87 | 4.64 | 12.0 | 127.07 | 4.84 | 0.82 |
| 4 | 10.0 | 372.93 | 5.92 | 8.0 | 298.05 | 5.70 | 1.25 |
| 5 | 14.0 | 107.71 | 4.68 | 16.0 | 147.84 | 5.00 | 0.73 |
| 6 | 13.0 | 244.87 | 5.50 | 15.0 | 315.48 | 5.75 | 0.78 |
| 7 | 14.0 | 115.23 | 4.75 | 16.0 | 135.27 | 4.91 | 0.85 |
| 8 | 13.0 | 257.26 | 5.55 | 15.0 | 179.11 | 5.19 | 1.44 |
| 9 | 8.0 | 232.12 | 5.45 | 10.0 | 194.37 | 5.27 | 1.19 |
| 10 | 16.0 | 172.20 | 5.15 | 15.0 | 281.81 | 5.64 | 0.61 |
| 11 | 13.0 | 177.41 | 5.18 | 8.0 | 181.17 | 5.20 | 0.98 |
| 12 | 13.0 | 225.55 | 5.42 | 10.0 | 327.23 | 5.79 | 0.69 |
| 13 | 15.0 | 135.66 | 4.91 | 15.0 | 213.37 | 5.36 | 0.64 |
| 14 | 15.0 | 154.65 | 5.04 | 14.0 | 135.94 | 4.91 | 1.14 |
| 15 | 12.0 | 114.81 | 4.74 | 15.0 | 181.80 | 5.20 | 0.63 |
| 16 | 15.0 | 294.21 | 5.68 | 13.0 | 296.58 | 5.69 | 0.99 |
| 17 | 15.0 | 187.32 | 5.23 | 15.0 | 183.62 | 5.21 | 1.02 |
| 19 | 16.0 | 385.36 | 5.95 | 15.0 | 376.57 | 5.93 | 1.02 |
| 21 | 15.0 | 318.06 | 5.76 | 10.0 | 276.15 | 5.62 | 1.15 |
| 22 | 14.0 | 114.40 | 4.74 | 14.0 | 97.24 | 4.58 | 1.18 |
| 23 | 12.0 | 260.20 | 5.56 | 12.0 | 346.74 | 5.85 | 0.75 |
| 24 | 14.0 | 211.61 | 5.35 | 16.0 | 202.88 | 5.31 | 1.04 |
| 25 | 14.0 | 155.98 | 5.05 | 15.0 | 125.66 | 4.83 | 1.24 |
| 27 | 16.0 | 79.66 | 4.38 | 16.0 | 67.35 | 4.21 | 1.18 |
| 28 | 16.0 | 124.76 | 4.83 | 16.0 | 165.01 | 5.11 | 0.76 |
| 29 | 15.0 | 225.58 | 5.42 | 10.0 | 164.02 | 5.10 | 1.38 |
| 30 | 14.0 | 166.54 | 5.12 | 15.0 | 165.41 | 5.11 | 1.01 |
| 31 | 15.0 | 134.14 | 4.90 | 14.0 | 135.19 | 4.91 | 0.99 |
| 33 | 13.0 | 282.10 | 5.64 | 16.0 | 275.33 | 5.62 | 1.02 |
| 34 | 10.0 | 118.88 | 4.78 | 15.0 | 155.15 | 5.04 | 0.77 |
| Mean | 13.7 | 195.00 | 5.19 | 13.5 | 208.90 | 5.27 | 0.96 |
| SD | 1.9 | 80.09 | 0.41 | 2.5 | 80.27 | 0.41 | 0.23 |
| CV | 13.8 | 41.07 | 7.83 | 18.3 | 38.43 | 7.73 | 24.25 |
| Median | 14.0 | 180.88 | 5.20 | 15.0 | 182.71 | 5.21 | 0.99 |
| Geo Mean | 13.5 | 180.09 | 5.18 | 13.3 | 193.65 | 5.25 | 0.93 |

Test/Ref Ratio
Ratio of Means %                93.35
Ratio of Geo Means %            93.00
Avg of Individual Ratios        0.96
90% C.I.                        86%-99%
Intra-CV                        16.07%

Fig. 10C

CHRONOTHERAPEUTIC DILTIAZEM FORMULATIONS AND THE ADMINISTRATION THEREOF

FIELD OF INVENTION

This invention relates to once daily preparations comprising Diltiazem and pharmaceutically acceptable salts thereof, such as the hydrochloride salt, suitable for evening administration to patients suffering hypertension and/or angina. This invention also relates to a method for evening administration of such once daily preparations to patients for the treatment and prevention of the patients' myocardial ischemia and angina.

BACKGROUND OF THE INVENTION

Diltiazem, a benzothiazepine, is an orally active calcium channel blocker (calcium-antagonist) with relatively high selectivity for vascular smooth muscle that is effective in the treatment of hypertension and angina pectoris. Today, persons having these conditions take prescribed once daily preparations of Diltiazem generally to maintain constant levels of the drug in the body over a 24-hour period. Until recently the timing of the taking of the medicine wasn't considered an important consideration by the medical community. Doctors generally did not take into account the natural circadian variation in the body's physiological functions. Researchers have now found that the timing of the taking of a medicine can affect the way the human body responds to the medicine. The science of treating the human body taking into account the natural circadian variation is Chronotherapeutics. Chronotherapeutics relies on the practice of delivering the correct amount of medication to the correct site of action at the most appropriate time period for the particular disease or condition.

In man, blood pressure does not remain constant during day and night. Early in the morning blood pressure begins to rise from the low levels reached during sleep. Increases in blood pressure are accompanied by increases in heart rate caused by the chemicals generated by the body and delivered into the blood stream. Epidemiological studies have indicated that the greatest incidence of heart problems such as stroke, heart attack, myocardial ischemia and sudden cardiac death occur during the early morning waking hours when the blood pressure is rising in response to the natural circadian rhythm. After normally rising in the morning, blood pressure remains elevated during the day until generally early evening when it starts to fall to its lowest level during sleep.

In one study, evening medication with Diltiazem for treatment of hypertension for effect the next morning has been stated to be more efficacious than other dosage schedules. *Administration Time—Dependent Effects of Diltiazem on The 24-Hour Blood Pressure Profile of Essential Hypertension Patients*, Isao Kohno et al. (Chronobiology International 14(1), 71-84, (1997.) In the report of the study, Herbesser R™ (200 mg) was identified as the Diltiazem preparation. Herbesser R™ is a Diltiazem formulation comprising a mixture of immediate release diltiazem—containing microspheres and sustained release diltiazem—containing coated microspheres. According to the report, following a single dose (200 mg) administration, the time of peak plasma diltiazem concentration occurred at 12.5 hours after administration. The peak plasma diltiazem concentration Cmax in the persons studied was 107 mg/ml. Following multiple dosages of 200 mg Diltiazem given over 7 days, the time of peak plasma diltiazem concentration (Cmax) was at 10 hours after administration. Cmax was 154 mg/ml.

However a careful review of the report shows inconsistencies which cannot support the authors' conclusions. Particularly at page 80, the best results shown in the graph are with respect to morning treatment with this formulation. Moreover at page 82, the authors themselves acknowledge the study cannot lead to reliable conclusions "because the number of patients was too small". Further, an immediate release portion of the dosage in the order of 15% is not desirable for evening administration. When the blood pressure is naturally at its lowest, not only is there no need for further reduction at that time, but such reduction can harm the patient. Particularly, if the blood pressure is reduced below a minimum the patient is put at a greater risk for cardiovascular accidents including stroke. Further, the 15% immediate release diltiazem is no longer available when needed.

In *A comparative study of the steady-state pharmacokinetics of immediate-release and controlled-release diltiazem tablets*, O. R. Leeuwenkamp et al., Eur. J. Clin. Pharmacol (1994) 46:243-247, controlled release properties and relative systemic availabilities of two dosages of the same controlled release diltiazem tablet formulation were studied by comparing them as steady state with those of an immediate release formulation. In the testing, the diltiazem plasma concentration increased slowly from about 6 hours after the evening dose of both CR tablets (Diltiazem CR 90 mg and Diltiazem CR 120 mg) resulting in relatively high plasma concentrations in the early morning hours. The clinicians concluded that twice-daily treatment with diltiazem CR tablets can replace thrice-daily treatment with a conventional diltiazem IR tablet. According to the clinicians "The early morning rise of the diltiazem plasma concentration, which might lead to a lower incidence of ischemic events, may be an important clinical advantage of both CR tablets."

On Apr. 22, 1998, Searle Canada announced that its Chronovera (R) (controlled onset extended-release verapamil) a high blood pressure medication was now available in Canada. Chronovera (R) was, according to Searle Canada, specifically designed to work with the body's natural circadian variations and was designed to be taken once-a-day just before bedtime. Chronovera provided 24-hour blood pressure control but was designed to deliver peak concentrations of verapamil in the morning when the blood pressure, heart rate and incidence of cardiovascular events were highest. According to Searle Canada, simply changing the time you take the drug your physician has prescribed will not provide the same safety and effectiveness that is designed specially for chronotherapy using verapamil. According to Searle Canada, its Chronovera (R) is unlike traditional medications including extended-release (XL) and sustained-release (SR) formulations which are usually prescribed in doses that maintain relatively constant levels of the drug in the body over a 24-hour period or attempt to maintain relatively constant levels of the drug in the body over a 24-hour period. According to Searle Canada, the prior formulations do not take into account the natural circadian variations in the body's physiological functions.

Sustained-release, once-daily diltiazem formulations have been taught which may be considered the traditional medication (according to Searle Canada). They appear not to give the benefits meant to be achieved by chronotherapy. For example, in *Pharmacokinetic Properties and Antihypertensive Efficacy of Once-Daily Diltiazem*, J. G. Kelly et al., Journal of Cardio-Vascular Pharmacology, 17:6:957-963, (1991), the controlled-release formulation of diltiazem released a proportion of the diltiazem relatively rapidly with the remainder released over a period extending to 24-hours. During in vitro dissolution testing 15% of the diltiazem in the dosage form was released in the first two hours, 54% was released in the first six hours, 89% in the first 13 hours and all of the remainder was released between 13 and 24 hours after administration. The diltiazem capsules contained either 120 mg or 240 mg of diltiazem. It should be noted that no difference is shown between the placebo and dosages in the article at wake-up (between 5:00 a.m. and 8:00 a.m.).

U.S. Pat. No. 4,960,596 discloses slow release 12 hour diltiazem formulations whose dissolution, when measured in accordance with United States Pharmacopoeia 21, purports to be within broad limits (between 5% and 35% after one hour, between 15% and 40% after two hours, between 20% and 50% after three hours, between 30% and 75% after four hours, between 40% and 80% after six hours and between 55% and 95% after eight hours). The examples in the patent, however, provide more specific range limitations specifying range limitations for the formulations exemplified such as at column 4, lines 8-10 and column 5, lines 60-62. In the first series of examples the release into aqueous medium was measured using the method of USP No. 21 of 10%-20% after one hour, 30%-35% after four hours and 60%-75% after eight hours. In the later examples, the release into aqueous medium was measured using the method of USP No. 21 at 15%-35% after one hour, 55%-75% after four hours, 75%-95% after eight hours. These formulations were, however, twice a day (b.i.d.) formulations.

A series of patents have issued to Elan Corporation p.l.c. involving controlled absorption diltiazem pellet formulations for oral administration in which each pellet has a core comprising diltiazem or a pharmaceutically acceptable salt thereof in association with a specified organic acid covered by an outer membrane which permits release of diltiazem from aqueous medium in accordance with U.S. Pharmacopoeia XX (Paddle Method) in buffered media at pH 1.5, pH 4.0 and pH 7.0. These are U.S. Pat. Nos. 4,721,619; 4,891,230; 4,894,240; 4,917,899; 5,002,776; 5,219,621; 5,336,504; 5,364,620 and 5,616,345. In U.S. Pat. No. 4,721,619, dissolution rates of the pellets of examples are found at column 4, lines 41-49 and column 5, lines 5-12. The formulations, however are for 12 hour. The formulations of U.S. Pat. No. 4,891,230 are also for administration every 12 hours.

U.S. Pat. No. 4,894,240 purports to provide formulations for once-daily administration and specifies a general dissolution pattern at column 2, lines 43-52 and a more restricted dissolution pattern at column 3, lines 3-12. The dissolution rates are determined according to U.S. Pharmacopoeia XXI in 0.05M KCl at pH 7.0 and at 100 r.p.m. The examples of the patent, however, provide a more limited dissolution pattern under U.S. Pharmacopoeia XXI (Paddle Method) at column 7, lines 30-34 and 47-51, at column 8, lines 16-20, 32-36 and 49-53 and at column 8, line 66-column 9, line 5. Similar examples are provided at columns 9, 10, 11 and 12. Nothing is taught with respect to formulations suitable as chronotherapeutics.

U.S. Pat. Nos. 4,917,899, 5,364,620 and 5,616,345 are to the same effect. So are the remaining Elan patents. Nothing in these patents teach formulations suitable as chronotherapeutics.

U.S. Pat. No. 5,529,790 purports to teach a delayed sustained-release pharmaceutical preparation in which a water-soluble drug core is surrounded by a hydratable diffusion barrier which delays drug release for about two to ten hours. While diltiazem hydrochloride dissolution patterns were provided in accordance with the U.S.P. basket dissolution method specified, no Cmax or the timing of the maximum blood levels is provided. The dissolution rates of the active are not appropriate for a suitable chronotherapeutic (see also U.S. Pat. Nos. 5,376,384 and 5,478,573).

U.S. Pat. Nos. 5,288,505 and 5,529,791 relate to extended-release galenical formulations of diltiazem or pharmaceutically acceptable salts thereof which comprise beads in which the active ingredient is in association with a wetting agent and which beads are coated by a microporous membrane. The Cmax of some formulations given in the patents provide for a Cmax after about 8-12 hours. Where the dosing of the formulations of the patents yields maximum diltiazem blood plasma levels (Cmax) of about 145 ng/ml, the Cmax is at about or less than 8 hours.

The applicants are also aware of a formulation marketed under the trade mark Tiazac™ a diltiazem HCl 24-hour sustained-release formulation based on teachings of U.S. Pat. Nos. 5,529,791 and 5,288,505.

Following chronic administration of Tiazac (240 mg once daily), the average peak plasma Diltiazem concentration (Cmax) is 183 ng/ml (multiple dosage) which occurred after about 7 hours past dose administration. Tiazac™ provides a bioavailability of approximately 59% of the total Diltiazem in the first 12 hours and 41% in the second 12 hours (after 12 hours, 59%; after 16 hours 77% and after 20 hours 90%).

In an article entitled *Effect of Morning Versus Evening Dosing of Diltiazem on Myocardial Ischemia Detected by Ambulatory Electrocardiographic Monitoring in Chronic Stable Angio Pectoris*, PRA KASH, C. Deedwanian et al., The American Journal of Cardiology, Vol. 80, Aug. 15, 1997, p. 421-425, the authors compare a.m. and p.m. dosing without using an appropriate dosage form for p.m. The Tmax is achieved between 2-6 hours at steady state.

In an article *The influence of Time Administration on the Pharmacokinetics of a Once A Day Diltiazem Formulation: Morning Against Bedtime*, Jean Thiffault et al., Biopharmaceutics & Drug Disposition, Vol. 17, 107-115 (1996), the once-a-day diltiazem formulation given at 2200 hours for seven days gave according to the article "significantly higher plasma concentrations of diltiazem in the early morning hours when the incidence of cardiovascular events is higher". The diltiazem dosages comprise 240 mg taken at 10:00 p.m. (22:00 hours) and maximum concentrations (Cmax) were achieved of 120 ng/ml after about six-eight hours of dosing. Unfortunately, the proposed system covers only the period from 2:00 a.m. to 8:00 a.m. To be a true chronotherapeutic, the time period covered should be between about 6:00 a.m. and noon. Moreover, this formulation when given at night leads to significantly lower bioavailability than if given in the morning.

In the article *Effect of Morning Versus Evening Dosing of Diltiazem on Myocardial Ischemia Detected by Ambulatory Electrocardiographic Monitoring in Chronic Stable Angio Pectoris*, PRA KASH, C. Deedwanian et al., The American Journal of Cardiology, Vol. 80, Aug. 15, 1997, p. 421-425, the authors report that both AM and PM administration of 480 mg Dilacor XR decreased the duration and number of episodes of myocardial ischemia in patients with chronic stable angina based on the 48-hour ambulatory electrocardiographic monitoring (AEM). There was no statistically significant difference between the two groups. However, the AM group demonstrated a 50% decrease in duration and a 70% decrease in number of episodes of myocardial ischemia compared to the PM group.

It is therefore an object of this invention to provide diltiazem preparations suitable for once-a-day administration in the evening for providing effective dosage amounts in the blood of diltiazem in the morning when blood pressure begins to rise from the low levels reached during sleep, so as to be suitable as a chronotherapeutic preparation.

It is a further object of this invention to provide a method of administration of the diltiazem preparations suitable as a chronotherapeutic so as to be effective in the morning at a time when the patient has most need of the diltiazem preparation.

Further and other objects of the invention will be realized by those skilled in the art from the following summary of the invention and detailed description of embodiments thereof.

SUMMARY OF THE INVENTION

According to one aspect of the invention, there is provided a controlled-release Galenical preparation (such as a tablet and a capsule) of pharmaceutically acceptable Diltiazem including the pharmaceutically acceptable salts thereof, such as the hydrochloride salt, suitable for evening dosing every 24 hours containing from about 120 mg to about 540 mg or more (as desired) of the form of Diltiazem associated with excipients to provide controlled (sustained) release of the form of Diltiazem for providing a Cmax of Diltiazem in the blood at between about 10 hours and about 15 hours (preferably about 11-about 13 hours) after administration, the preparation comprising the form of Diltiazem in oral sustained-release dosage form in which the Diltiazem is adapted to be released after administration over a prolonged period of time and the preparation is adapted to release the Diltiazem (i) into an aqueous medium at the following rates measured using the method of United States Pharmacopoeia No. XXIII (at 100 rpm in 900 ml of water):
  (a) between about 1% and about 15% after about 2 hours, preferably between about 4% and about 8% after 2 hours;
  (b) between about 7% and about 35% after about 4 hours preferably between about 16% and about 21% after 4 hours;
  (c) between about 30% and about 58% after about 8 hours preferably between about 44% and about 52% after 8 hours;
  (d) between about 55% and about 80% after about 14 hours preferably between about 69% and about 76% after about 14 hours; and
  (e) in excess of about 75% after about 24 hours and preferably more than about 85% after 30 hours.

and/or (ii) into a buffered medium (such as, for example, phosphate buffer (U.S.P.)) having a pH between about 5.5 and about 6.5, preferably about 5.8 at the following rates measured using the method of United States Pharmacopoeia No. XXIII at 100 rpm in 900 ml of the buffered medium:
  (a) between about 1% and about 25% after about 2 hours, preferably between about 4% and about 15% after 2 hours;
  (b) between about 7% and about 45% after about 4 hours preferably between about 16% and about 30% after 4 hours;
  (c) between about 30% and about 68% after about 8 hours preferably between about 44% and about 62% after 8 hours;
  (d) in excess of about 75% after about 24 hours and preferably more than 80% after 24 hours.

Preferably no initial retard or delay is built into the preparation retarding/delaying release of Diltiazem from the preparation. Preferably the release rate from the preparation of the Diltiazem is less than about 15% of the total active per hour during dissolution. The preparation may be a diffusion controlled preparation such as, for example, a preparation incorporating the use of microgranules found, for example, in capsules and tablets; tablets; and coated tablets.

The preparation may comprise a plurality of microgranules or pellets, each microgranule comprising a central core or bead containing the form of diltiazem coated with a microporous membrane. The microgranules or pellets may be included in a capsule, which dissolves when swallowed to release the microgranules or pellets. The preparation may also comprise a tablet in which the microgranules have been compressed to form the tablet. When compressed into tablet form, wax placebo beads (as known by persons skilled in the art) are preferably included to absorb the shock placed on the microgranules (core and membrane) during the tableting process. By doing so, the integrity of the microgranules containing the Diltiazem active remains intact and the release rate from the preparation is not affected. The tablet may also be coated or uncoated. The preparation may also comprise a sustained-release tablet coating from which preparation the Diltiazem is released. In this regard, the sustained release coating may be applied (sprayed onto) to each tablet.

Where the preparation comprises microgranules or pellets (for example) in the capsule or tablet (made, for example, by compressing the microgranules (with preferably wax placebo beads)), the central core may comprise Diltiazem or a pharmaceutically acceptable salt thereof associated with a wetting agent. The Diltiazem may be mixed (in whole or in part) with the wetting agent or may not be mixed with the wetting agent. The wetting agent assists to maintain the solubility of the Diltiazem in each microgranule, ensuring that the solubility of the Diltiazem is unaffected by the pH of the gastrointestinal tract or other adverse conditions which each of the microgranules of the preparation will meet in the gastrointestinal tract.

If the Diltiazem and/or pharmaceutically acceptable salt is not mixed with the wetting agent then the microporous membrane should comprise with suitable adjuvants, a water-dispersible or water-soluble polymer (such as HPMC) and a water-, acid- and base-insoluble polymer of a neutral acrylic polymer such as Eudragit NE30D (a neutral copolymer of acrylic acid ethyl ester and acrylic acid methyl ester) which hydrates the microgranule (including core). If the composition comprises a mixture of the Diltiazem and/or pharmaceutically acceptable salt with the wetting agent, the microporous membrane is preferably the same. However, it may also comprise any suitable membrane which gives to the preparation the required dissolution characteristics.

In this regard, the preferred microporous membrane comprises Eudragit NE30D and hydroxypropylmethylcellulose. This membrane will hydrate the core within the microporous membrane which, for example, may contain diltiazem surrounding a neutral pellet of sugar. The Eudragit NE30D in the membrane expands when it encounters gastrointestinal fluid to greater than 365% of its original size (elongation). This expandability of the membrane gives it the ability to hydrate the membrane and core. The mechanism of release is postulated to be that the membrane will swell while the fluids penetrate and hydrate the core and dissolve the diltiazem and wetting agent. This mechanism is, it is thought, driven by the concentration gradient through the membrane (high concentration inside and low concentration outside).

When Eudragit RS and Eudragit RL are combined to form the microporous membrane, the membrane can expand only very little before breakage or fracturing. The reason is that Eudragit RS expands minimally (about 6%) before the membrane material breaks or fractures changing its release mechanism from the core. Thus, the mechanism of release from this membrane is thought to be by "washing" the diltiazem through pores created when a plasticizer incorporated in the membrane is released in the gastrointestinal fluid. The diltiazem at the outer surface of the core would be washed from the core through the pores of the microporous membrane, then the diltiazem next presenting itself to the fluids after "washing" of the uppermost (outermost) diltiazem, and so on.

Instead of the wetting agent, any other suitable dissolution agent may be used to assist the release of the Diltiazem from the preparation. For example, instead of the preferred surface active (wetting) agent (surfactant), an organic acid (such as adipic acid, ascorbic acid, citric acid, fumaric acid, malic acid, succinic acid, tartaric acid and the like) may be incorporated in the core. In this regard, the presence of the organic acid in the core permits the diltiazem in the core to dissolve when the composition passes into the higher pH regions of the gastrointestinal tract of the intestine at which pH diltiazem is much less soluble.

One of the membranes, which may be used (though not preferred) is the combination of Eudragit RS and Eudragit RL disclosed in U.S. Pat. No. 4,721,619. (See column 1, lines 55-68 and column 2, lines 44-68.) The '619 patent also mentions the use of hydroxypropylmethylcellulose as a water-soluble membrane. The mechanism of release in this case is not by hydration of the core but rather by "washing" the Diltiazem through the pores created in the membrane (for example when the plasticizer in the membrane is released in the gastrointestinal fluid).

The Diltiazem may be present in the core in, for example, the hydrochloride salt form, in which event no dissolution agent may be required in the core. Suitable preparations such as capsules of the microgranules making up the total Diltiazem active present, may comprise, in the core, Diltiazem hydrochloride between about 50% and about 85% (% w/w of the total preparation (for example, about 69% to about 73%)), a wetting agent (such as sucrose stearate) between about 2% and about 25% (% w/w of the total preparation) (for example about 7% to about 8%) together with suitable adjuvants in the core, and in the membrane between about 0.1% and about 2% of the total preparation of water-soluble and/or water-dispersible polymer such as hydroxypropylmethylcellulose (for example about 0.3% to about 0.6%), and between about 5% and about 20% (% w/w of the preparation) of a neutral copolymer of acrylic acid ethyl ester and acrylic acid methyl ester (such as Eudragit NE30D) (for example about 7% to about 11%).

The microgranules may also be compressed into tablets using suitable excipients. The percentages may be as described above. The tablets may be manufactured, as discussed above, using the microgranules with wax placebo beads and compressing the combination into tablets in the presence of, for example, hydrogenated vegetable oil, sodium starch glycolate and silicone dioxide which have been blended with the microgranules and wax placebo beads before tableting. The tablets may then be coated or uncoated.

According to another aspect of the invention, there is provided a controlled-release Galenical preparation (such as a tablet and a capsule) of pharmaceutically acceptable Diltiazem including the pharmaceutically acceptable salts thereof, such as the hydrochloride salt, suitable for evening dosing every 24 hours containing from about 120 mg to about 540 mg or more (as desired) of the form of Diltiazem associated with excipients to provide controlled (sustained) release of the form of Diltiazem for providing a Cmax of Diltiazem in the blood at between about 10 hours and about 15 hours (preferably about 11-about 13 hours) after administration, the preparation comprising the form of Diltiazem in oral sustained-release dosage form in which the Diltiazem is adapted to be released after administration over a prolonged period of time and exhibits when given to humans (i) a higher bioavailability when given at night compared to when given in the morning without food according to FDA guidelines or criteria and (ii) bioequivalence when given in the morning with food (such as a standardized FDA breakfast) and without food according to the same FDA guidelines or criteria.

The FDA guidelines are those entitled:

"GUIDANCE ORAL EXTENDED (CONTROLLED) RELEASE DOSAGE FORMS IN VIVO BIOEQUIVALENCE AND IN VITRO DISSOLUTION TESTING" prepared under 21 CFR 10.90(b)(9) by Shrikant V. Dighe, Ph.D., Director, Division of Bioequivalence Office of Generic Drugs dated Sep. 3, 1993 and concurred by Roger L. Williams, M.D., Director, Office of Generic Drugs, Center for Drug Development Research dated Sep. 4, 1993 which is incorporated herein by reference; and "GUIDANCE STATISTICAL PROCEDURES FOR BIOEQUIVALENCE STUDIES USING A STANDARD TWO-TREATMENT CROSSOVER DESIGN" prepared under 21 CFR 10.90(b)(9) by Mei-Ling Chem, Ph.D., Division of Bioequivalence Review Branch II dated Jun. 12, 1992 and Rabindra Patnaik, Ph.D., Division of Bioequivalence Review Branch II dated Jun. 26, 1992, approved by Shrikant V. Dighe, Ph.D., Director, Division of Bioequivalence dated Jun. 29, 1992 and concurred by Roger L. Williams, M.D., Director, Office of Generic Drugs dated Jun. 29, 1992 which is incorporated herein by reference.

In small part the said "GUIDANCE" documents provide as follows:

Pharmacokinetic Analysis of Data: Calculation of area under the plasma concentration-time curve to the last quantifiable concentration ($AUC_{0-\tau}$) and to infinity ($AUC_{0-\infty}$), $C_{max}$, and $T_{max}$ should be performed according to standard techniques.

Statistical Analysis of Pharmacokinetic Data: The log transformed AUC and $C_{max}$ data should be analyzed statistically using analysis of variance. These two parameters for the test product should be shown to be within 80-125% of the reference product using the 90% confidence interval. See also Division of Bioequivalence Guidance Statistical Procedures for Bioequivalence Studies Using a Standard Two-Treatment Crossover Design.

Statistical Analysis of Pharmacokinetic Data: The log transformed AUC and $C_{max}$ data should be analyzed statistically using analysis of variance. These two parameters for the test product should be shown to be within 80-125% of the reference product using the 90% confidence interval. Fluctuation for the test product should be evaluated for comparability with that for the reference product. For further information on statistical analysis, see the Division of Bioequivalence Guidance Statistical procedures for Bioequivalence Studies Using a Standard Two-Treatment Crossover Design.

2. Multiple Dose Studies

At a minimum, the following pharmacokinetic parameters for the substance(s) of interest should be measured in a multiple dose bioequivalence study:

a. Area under the plasma/blood concentration-time curve from time zero to time τ over a dosing interval at steady state ($AUC_{0-\tau}$), where τ is the dosing interval.

b. Peak drug concentration ($C_{max}$) and the time to peak drug concentration ($T_{max}$), obtained directly from the data without interpolation, after the last dose is administered.

c. Drug concentrations at the end of each dosing interval during steady state ($C_{min}$).

d. Average drug concentration at steady state ($C_{av}$), where $C_{av}=AUC_{0-\tau}/\tau$.
e. Degree of fluctuation (CF) at steady state, where $DF=100\% \times (C_{max}-C_{min})/C_{av}$.

Evidence of attainment of steady state for the test and reference products should be submitted in the bioequivalence study report.

B. Statistical Analysis

Parametric (normal-theory) general linear model procedures are recommended for the analysis of pharmacokinetic data derived from in vivo bioequivalence studies. An analysis of variance (ANOVA) should be performed on the pharmacokinetic parameters AUC and $C_{max}$ using General Linear Models (GLM) procedures of SAS (4) or an equivalent program. Appropriate statistical models pertaining to the design of the bioequivalence study should be employed. For example, for a conventional two-treatment, two-period, two-sequence (2×2) randomized crossover study design, the statistical model often includes factors accounting for the following sources of variation:

1. Sequence (sometimes called Group or Order)
2. Subjects, nested in sequences
3. Period (or Phase)
4. Treatment (sometimes called Drug or Formulation)

The sequence effect should be tested using the [subject (sequence)]mean square from the ANOVA as an error term. All other main effects should be tested against the residual error (error mean square) from the ANOVA. The LSMEANS statement should be used to calculate least squares means for treatments. The ESTIMATE statement in SAS should be used to obtain estimates for the adjusted differences between treatment means and the standard error associated with these differences. The two one-sided hypotheses at the $\alpha=0.05$ level of significance should be tested for AUC and $C_{max}$ by constructing the 90% confidence interval for the ratio between the test and reference averages.

III. LOGARITHMIC TRANSFORMATION OF PHARMACOKINETIC DATA

A. Statistical Assumptions

The assumptions underlying the ANOVA are (5):
1. Randomization of samples
2. Homogeneity of variances
3. Additivity (linearity) of the statistical model
4. Independency and normality of residuals In bioequivalence studies, these assumptions can be interpreted as follows:

1. The subjects chosen for the study should be randomly assigned to the sequences of the study.
2. The variances associated with the two treatments, as well as between the sequence groups, should be equal or at least comparable.
3. The main effects of the statistical model, such as subject, sequence, period and treatment effect for a standard 2×2 crossover study, should be additive. There should be no interactions between these effects.
4. The residuals of the model should be independently and normally distributed. In other words, data from bioequivalence studies should have a normal distribution.

If these assumptions are not met, additional steps should be taken prior to the ANOVA including data transformation to improve the fit of the assumptions or use of a nonparametric statistical test in place of ANOVA. However, the normality and constant variance assumptions in the ANOVA model are known to be relatively robust, i.e., small or moderate departure from each (or both) of these assumptions will not have a significant effect on the final result.

B. Rationale for Log Transformation

1. Clinical Rationale

In a meeting in September 1991, the Generic Drugs Advisory Committee (GDAC) concluded that the primary comparison of interest in a bioequivalence study was the ratio rather than the difference between average parameter data from the test and reference formulations. Using log transformation, the general linear statistical model employed in the analysis of bioequivalence data allows inferences about the difference between the two means on the log scale, which can then be retransformed into inferences about the ratio of the two averages (means or medians) on the original scale. Log transformation thus achieves the general comparison based on the ratio rather than the difference (6).

2. Pharmacokinetic Rationale

Westlake (7,8) observed that a multiplicative model is postulated for pharmacokinetic parameters in bioavailability/bioequivalence studies, i.e., AUC and $C_{max}$ (but not $T_{max}$). Assuming that elimination of the drug is first order and only occurs from the central compartment, the following equation holds after an extravascular route of administration:

$$AUC_{0-\infty} = FD/CL$$
$$= FD/(VK_e)$$

where F is the fraction absorbed, D is the administered dose, and FD is the amount of drug absorbed. CL is the clearance of a given subject which is the product of the apparent volume of distribution (V) and the elimination rate constant $(K_e)$.[2]

The use of AUC as a measure of the amount of drug absorbed thus involves a multiplicative term (CL) which might be regarded as a function of the subject. For this reason, Westlake contends that the subject effect is not additive if the data is analyzed on the original scale of measurement.

Logarithmic transformation of the AUC data will bring the CL $(VK_e)$ term into the equation in an additive fashion.

$$1nAUC_{0-\infty}=1nF+1nD-1nV-1nK_3$$

Similar arguments were given for $C_{max}$. The following equation applies for a drug exhibiting one compartmental characteristics:

$$C_{max}=(FD/V)xe^{-K_e \times T_{max}}$$

where again F, D and V are introduced into the model in a multiplicative manner. However, after logarithmic transformation, the equation becomes $$1nC_{max}=1nF+1ND-1NV-K_eT_{max}$$

Log transformation of the $C_{max}$ data also results in the additive treatment of the V term.

3. Statistical Rationale

Logarithmic transformation of the data from bioequivalence studies can be used to circumvent the use of estimates of the reference product average for computation of the confidence interval for the ratio of product averages. This is an advantage for the cases where a least squares estimate for the reference product mean is not well defined. Standard parametric methods are ill-suited to making inferences about the ratio of two averages, though some valid methods do exist (9). Log transformation changes the problem to one of making inferences about the difference (on the log scale) of two averages, for which the standard methods are well suited.

Many biological data correspond more closely to a log-normal distribution than to a normal distribution. The plasma concentration data including the derived parameters AUC and $C_{max}$ tend to be skewed, and their variances tend to increase with the means. Log transformation is likely to remedy this situation and make the variances independent of the mean. In addition, frequency distributions skewed to the left (with a long tail to the right) are often made more symmetrical by log transformation.

This argument is actually less persuasive than the argument based on the additivity of the statistical model because it is based largely on the between-subject distribution of AUC and $C_{max}$ values. For crossover studies, it is largely the within-subject distribution of values that determines the validity and efficiency of the standard parametric methods of analysis. p3 Despite the arguments regarding the effect of log transformation on normality of bioequivalence data, the division of Bioequivalence recognizes that the limited sample size (20-30 subjects) in a bioequivalence study precludes a reliable determination of the underlying normal distribution of the data set either with or without log transformation.

C. General Procedures

Based on the arguments in the preceding section, the Division of Bioequivalence recommends that the pharmacokinetic parameters AUC and $C_{max}$ be log transformed. Firms are not encouraged to test for normality of data distribution after log transformation, nor should they employ normality of data distribution as a justification for carrying out the statistical analysis on the original scale. Robustness of a balanced study to nonnormality of the data plus use of log transformation will be adequate in most cases.

If a firm believes that the data of a particular bioequivalence study should be statistically analyzed on the original scale rather than the log scale, justification based upon a sound scientific rationale, as well as the statistical methods to be used, ought to be submitted to and reviewed by the Division of Bioequivalence.

[2]Note that a more general equation can be written for any multi-compartmental model as $AUC_{0-\infty}=FD/(V_{d\beta}\lambda_z)$ where $V_{d\beta}$ is the volume of distribution relating drug concentration in plasma or blood to the amount of drug in the body during the terminal exponential phase, and $\lambda_z$ is the terminal slope of the concentration-time curve.

Thus, according to another aspect of the invention, the results of biostudies employing a formulation according to an embodiment of the invention, clearly show that when given at different times (P.M. or A.M. dosing) and under different conditions (with and without food) though they achieve their maximum bioavailability at the same $T_{max}$, when the formulation is given at night (no food) a higher bioavailability (for example a significantly higher bioavailability exceeding 25% ($C_{max}$) is attained than when given in the morning without food (according to FDA guidelines) and bioequivalence when given with food or without food in the morning according to the FDA guidelines.

According to another aspect of the invention, a method of treatment of a patient's hypertension and/or angina is provided comprising administration of a preparation of Diltiazem described above, to the patient in the evening for example at about 7:00-about 11:00 p.m. for effective treatment of the patient's hypertension and/or angina the next morning, for example between about 6:00 a.m. and about noon.

According to another embodiment of the invention a method of treatment of a patient's hypertension and/or angina is provided comprising administration of a preparation which exhibits a higher bioavailability (exceeding, for example, 25%) when given at night compared to when given in the morning without food according to FDA guidelines or criteria and bioequivalence when given with food (for example given a standardized FDA breakfast) and without food according to the same FDA guidelines or criteria. Thus a 24-hour diltiazem preparation is provided wherein the Cmax of diltiazem in the blood is provided from about 10-15 hours after administration of a single dosage to a patient or about 9-15 hours after multiple dosages over a number of days and displays the dissolution pattern described above determined according to USP 23, page 1791 using Apparatus 1. Apparatus 1 is described as consisting of the following:

a covered vessel made of glass or other inert, transparent material[1]; a motor; a metallic drive shaft; and a cylindrical basket. The vessel is partially immersed in a suitable water bath of any convenient size that permits holding the temperature inside the vessel at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is preferable. The vessel is cylindrical, with a hemispherical bottom. It is 160 to 175 mm high, its inside diameter is 98 to 106 mm, and its nominal capacity is 1000 mL. Its sides are flanged at the top. A fitted cover may be used to retard evaporation.[2] The shaft is positioned so that its axis is not more than 2 mm at any point from the vertical axis of the vessel and rotates smoothly and without significant wobble. A speed-regulating device is used that allows the shaft rotation speed to be selected and maintained at the rate specified in the individual monograph, within±4%.

[1] The materials should not sorb, react, or interfere with the specimen being tested.
[2] If a cover is used, it provides sufficient openings to allow ready insertion of the thermometer and withdrawal of specimens. (taken from USP 23)

Shaft and basket components of the stirring element are fabricated of stainless steel, type 316 or equivalent, to the specifications shown in FIG. 1. Unless otherwise specified in the individual monograph, use 40-mesh cloth. A basket having a gold coating 0.0001 inch (2.5 μm) thick may be used. The dosage unit is placed in a dry basket at the beginning of each test. The distance between the inside bottom of the vessel and the basket is maintained at 25±2 mm during the test.

According to another aspect of the invention, a method of treating and preventing myocardial ischemia and angina in a patient is provided comprising administration of a preparation of Diltiazem described above, to the patient in the evening for example at about 6:00-about 8:00 p.m. for effective treatment or prevention of the myocardial ischemia and angina the next morning, for example between about 7:00 a.m. and about 11:00 a.m.

According to another aspect of the invention, a method of treating and preventing myocardial ischemia and angina in a patient is provided comprising administration of a preparation of Diltiazem described above, to the patient in the evening for example at about 6:00-about 8:00 p.m. for effective treatment or prevention of the myocardial ischemia and angina over a twenty-four hour period.

According to another embodiment of the invention a method of treating myocardial ischemia is provided comprising administration of a preparation which exhibits a higher bioavailability (exceeding, for example, 25%) when given at night compared to when given in the morning without food according to FDA guidelines or criteria and bioequivalence when given with food (for example given a standardized FDA breakfast) and without food according to the same FDA guidelines or criteria.

Thus a 24-hour diltiazem preparation is provided wherein the Cmax of diltiazem in the blood is provided from about 10-17 hours after administration of a single dosage to a patient or about 9-15 hours after multiple dosages over a number of days and displays the dissolution pattern described above determined according to USP 23, page 1791 using Apparatus 1. Apparatus 1 is described as consisting of the following:
    a covered vessel made of glass or other inert, transparent material[1]; a motor; a metallic drive shaft; and a cylindrical basket. The vessel is partially immersed in a suitable water bath of any convenient size that permits holding the temperature inside the vessel at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is preferable. The vessel is cylindrical, with a hemispherical bottom. It is 160 to 175 mm high, its inside diameter is 98 to 106 mm, and its nominal capacity is 1000 mL. Its sides are flanged at the top. A fitted cover may be used to retard evaporation.[2] The shaft is positioned so that its axis is not more than 2 mm at any point from the vertical axis of the vessel and rotates smoothly and without significant wobble. A speed-regulating device is used that allows the shaft rotation speed to be selected and maintained at the rate specified in the individual monograph, within ±4%.

[1] The materials should not sorb, react, or interfere with the specimen being tested.
    [2] If a cover is used, it provides sufficient openings to allow ready insertion of the thermometer and withdrawal of specimens.

Shaft and basket components of the stirring element are fabricated of stainless steel, type 316 or equivalent, to the specifications shown in FIG. 1. Unless otherwise specified in the individual monograph, use 40-mesh cloth. A basket having a gold coating 0.0001 inch (2.5 µm) thick may be used. The dosage unit is placed in a dry basket at the beginning of each test. The distance between the inside bottom of the vessel and the basket is maintained at 25±2 mm during the test.

According to another aspect of the invention, where the preparations comprise cores wherein the diltiazem is in association with a wetting agent, the wetting agent may be selected from:
    sugars;
    saccharose, mannitol, sorbitol;
    lecithins;
    $C_{12}$ to $C_{20}$ fatty acid esters of saccarose, commercialized under the name of sucroesters (Gattefosse, France) or under the name of crodesters (Croda, U.K.) such as sucrose stearate marketed under the trade name of Crodesta;
    xylose esters or xylites;
    polyoxyethylenic glycerrides;
    esters of fatty acids and polyoxyethylene (Brijs, Renex and Eumulgines, Henkel, RFA);
    sorbitan fatty acid esters (Span, Atlas, U.S.A.);
    polyglycides-glycerides and polyglycides-alcohols esters (Gelucires, Gattefosse, France)
    Metal salts such as NaCl or sodium lauryl sulphate The microporous membrane may be of any suitable material or combination of materials known in the art. Where the wetting agent is in association with the diltiazem in the core and not mixed therewith, the microporous membrane should comprise a water-soluble or water dispersible polymer or copolymer such as hydroxypropylmethylcellulose and a water-, acid- and base-insoluble polymer such as a neutral copolymer of acrylic acid ethyl ester and acrylic acid methyl ester such as Eudragit NE30D. This enables the bead to be hydrated by the introduction of intestinal fluids into the bead hydrating the bead and therefore mixing the diltiazem and the wetting agent. The membrane itself, because of the fluids passing through the membrane, will swell. This membrane acts differently from membranes which do not swell. These other non-hydratable or swellable membranes may be made-up, for example, of water-soluble or water-dispersible polymers or copolymers and a water-, acid- and base-insoluble polymer such as Eudragit RS which swell less easily (owing to the reduced content in quaternary ammonium groups) and are only slightly permeable to active ingredients. This membrane is best suited for coating cores of Diltiazem mixed with a wetting agent or organic acid.

Among materials which may be used to make the microporous membranes, may be mentioned particularly polyacrylates and polymethacrylates of the Eudragit type, ethyl celluloses such as Ethocels from Dow U.S.A. and Aquacoat of FMC U.S.A., hydroxypropylmethylcellulose, hydroxyethylcellulose and hydroxypropylcellulose.

Additionally, adjuvants may be put in the formulation as required such as plastifying agents (plasticizer), pigments, fillers, lubricants and anti-foaming agents. For example talc and/or magnesium stearate may be used as a lubricant, dibutyl sebecate as plasticizer, titanium dioxide as a pigment, Tween 80 as an emulsifier and silicone oil as an anti-foaming agent. The amount of the microporous membrane is adjusted to provide the sustained release characteristics described.

Thus embodiments of the invention have higher bioavailability (greater AUC and $C_{max}$ at the same time (T)) when given at night than given in the morning without food according to the FDA guidelines discussed previously and are bioequivalent when given in the morning with food to formulation given in the morning without food according to the FDA guidance.

DETAILED DESCRIPTION OF EMBODIMENTS

The invention will now be illustrated with reference to the following examples and with reference to the following Figures:

FIG. 1: is a graph illustrating the Diltiazem Concentration (ng/mL) in the blood after a specified period after a single dose of a 300 mg Diltiazem capsule preparation made according to an embodiment of the invention.

Figure 2:
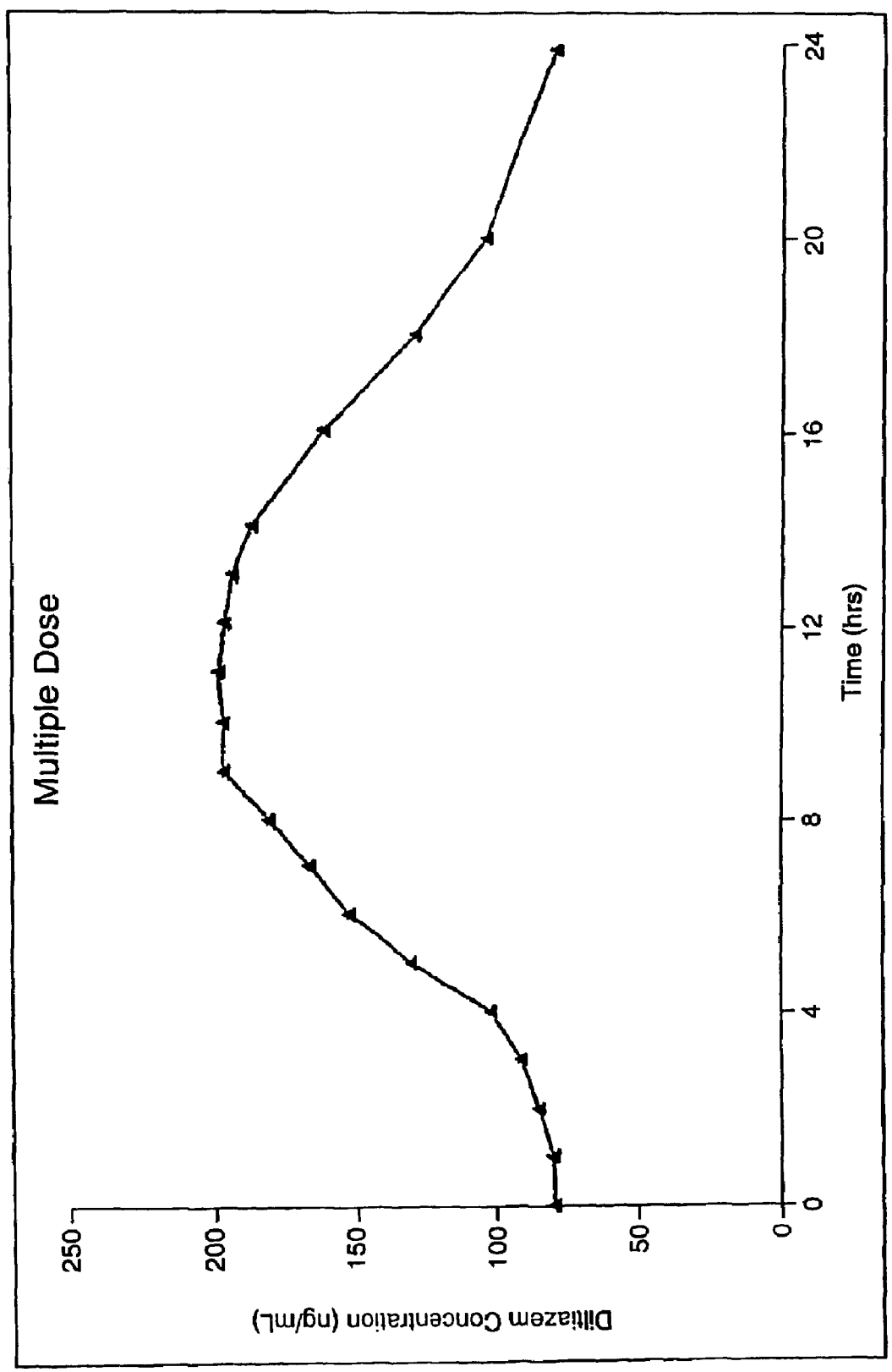

FIG. 2: is a graph illustrating the Diltiazem Concentration (ng/mL) in the blood over a 24-hour period after giving multiple doses of the same 300 mg Diltiazem capsules referred to with respect to FIG. 1 but over a number of days.

Figure 3:
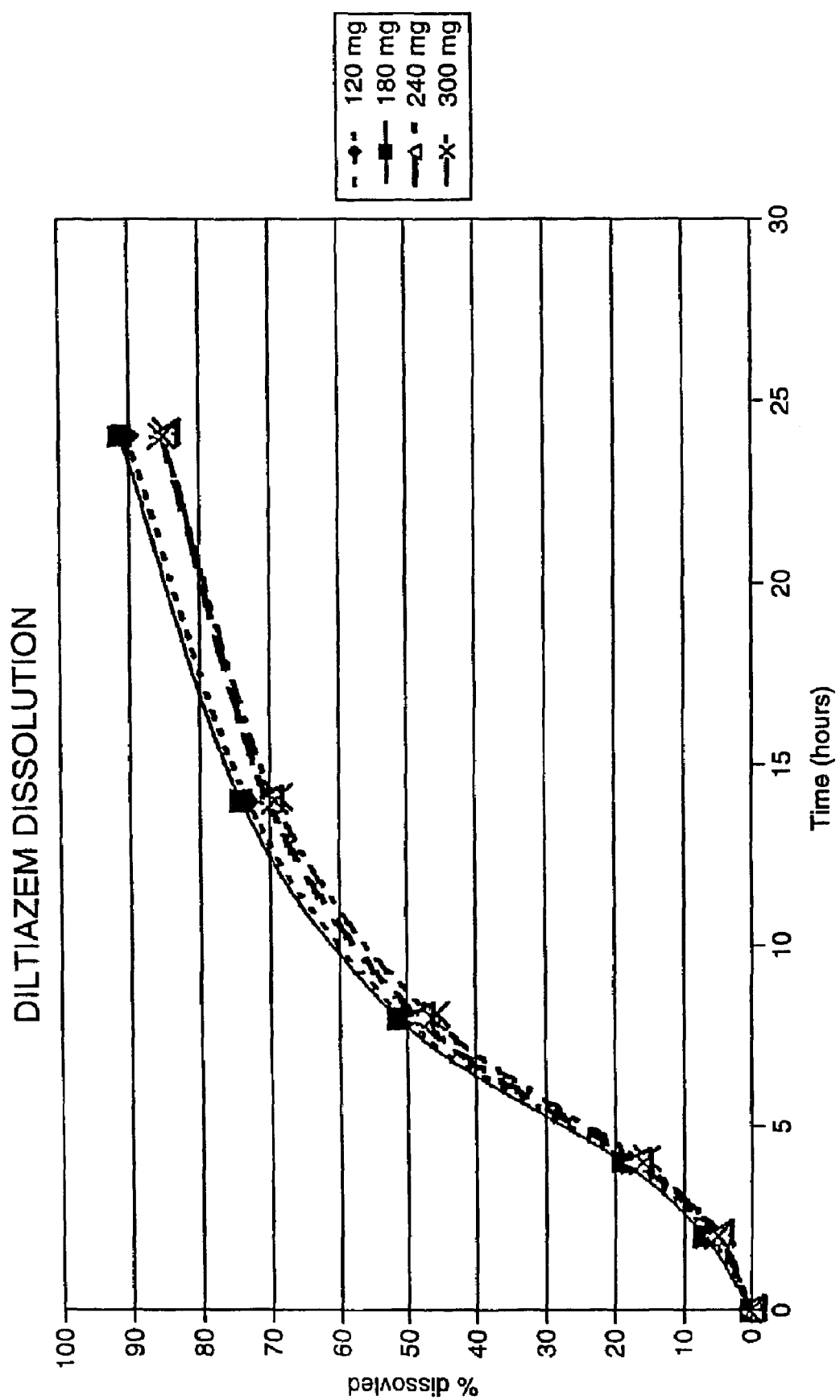

FIG. 3: is a graph illustrating dissolution profiles generated according to USP 23 using Apparatus 1 (baskets) at 100 r.p.m. in 900 ml of water for capsule preparations made according to embodiments of the invention (120 mg, 180 mg, 240 mg and 300 mg of Diltiazem active).

Figure 4:
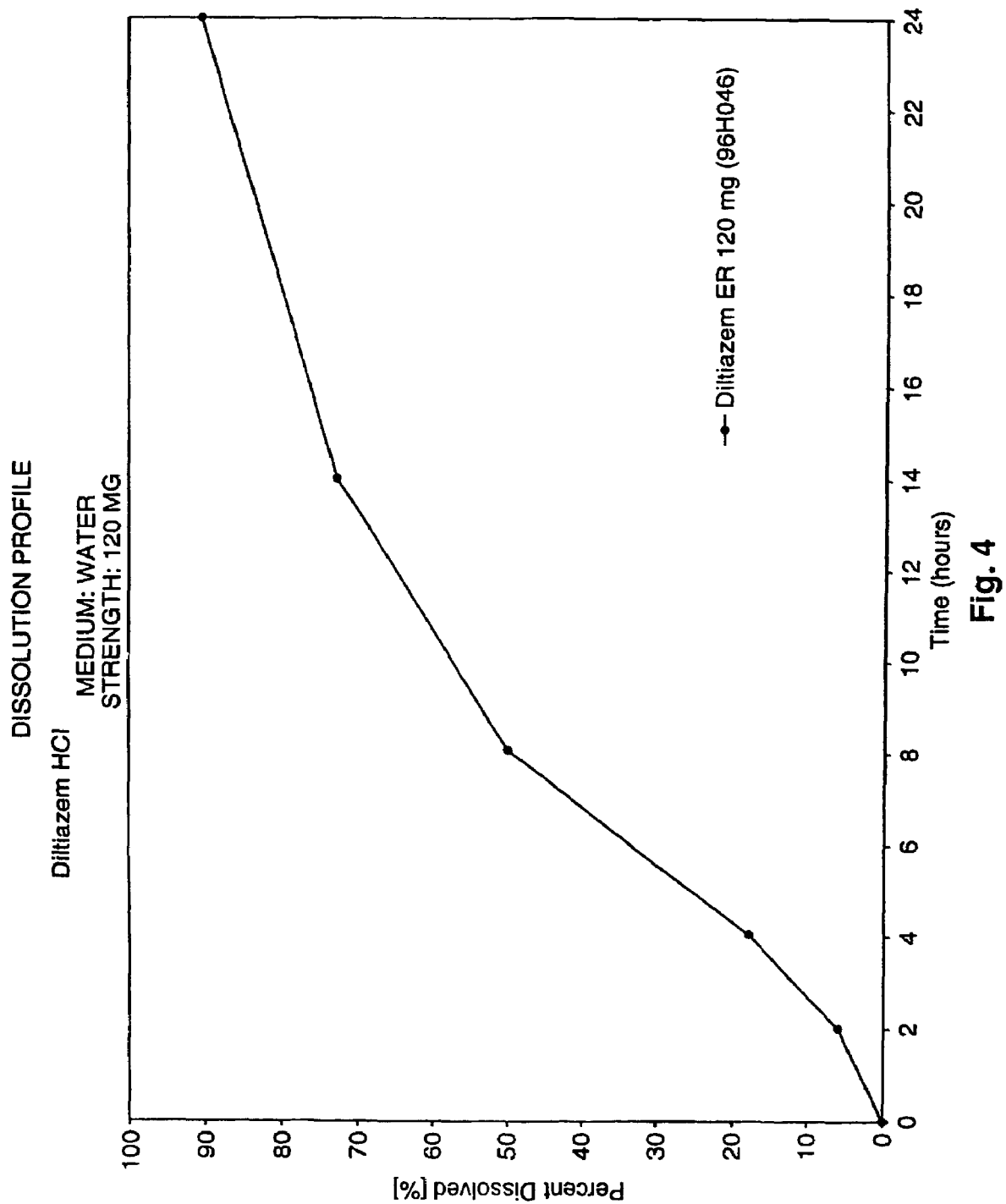

FIG. 4: illustrates the dissolution profile of a 120 mg capsule preparation of Diltiazem HCl in water according to USP 23 (Apparatus 1—baskets) according to an embodiment of the invention.

Figure 5:
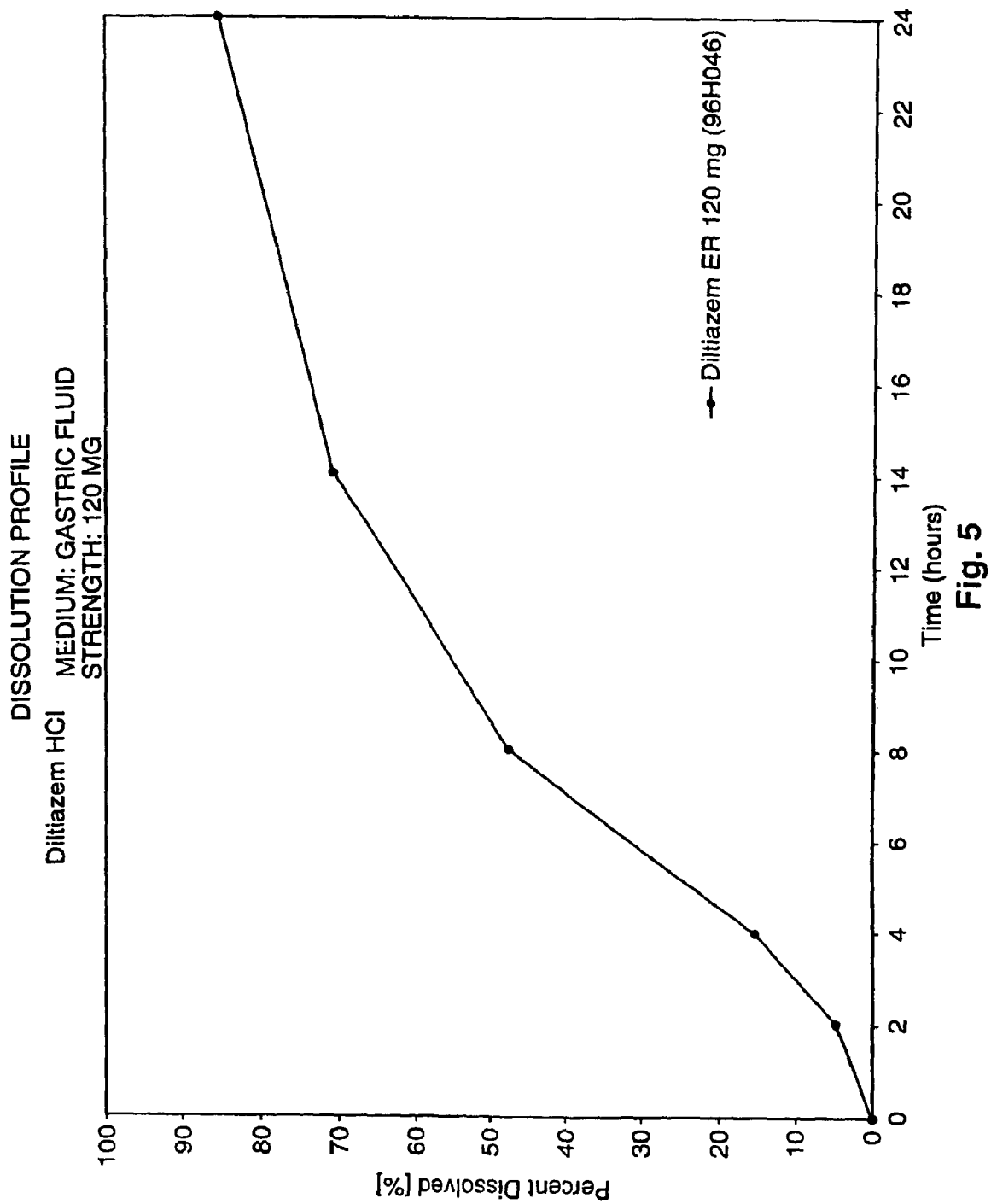

FIG. 5: illustrates the dissolution profile of a 120 mg capsule preparation of Diltiazem HCl in gastric fluid according to USP 23 (Apparatus 1—baskets) according to an embodiment of the invention.

Figure 6:
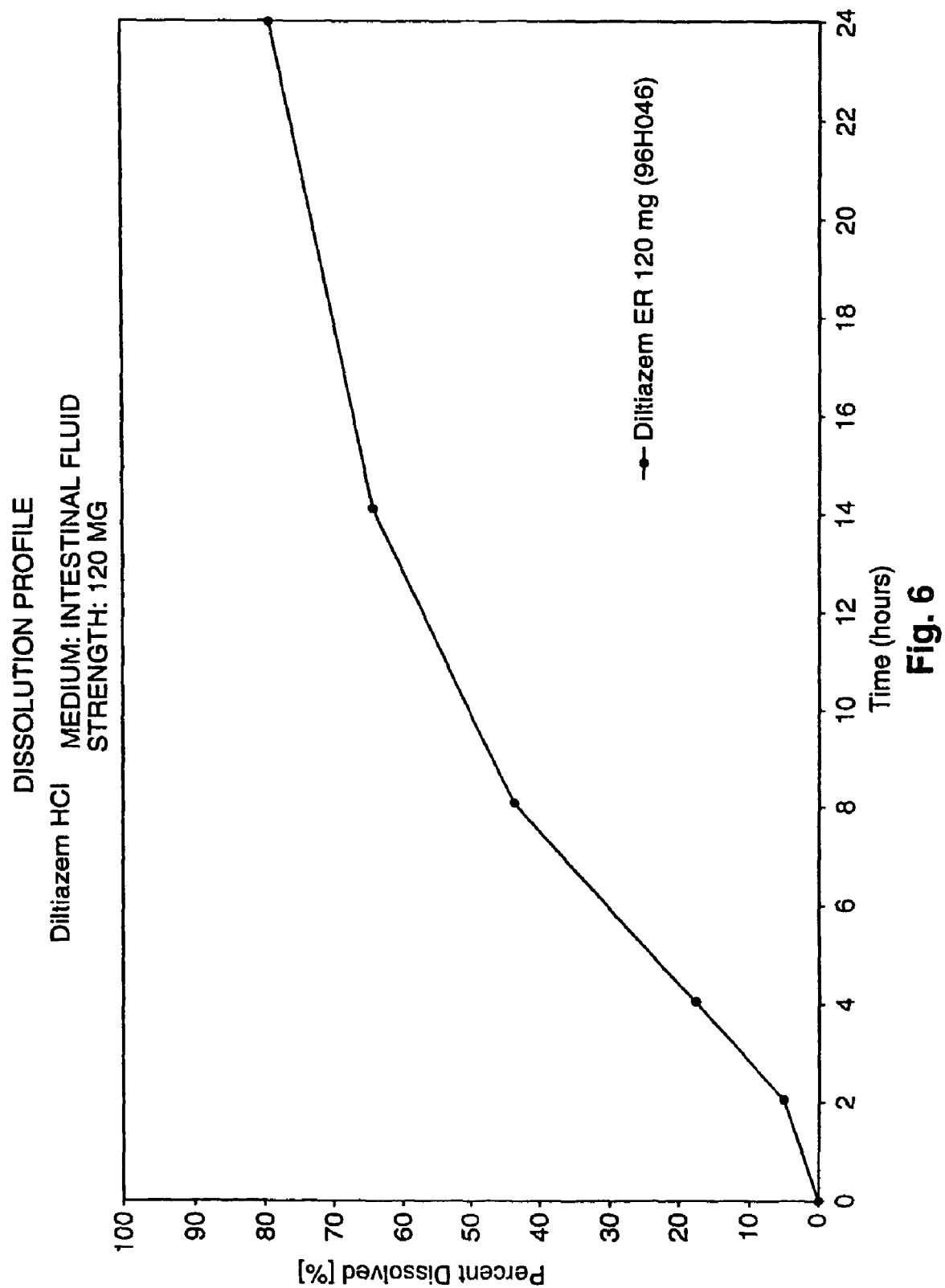

FIG. 6: illustrates the dissolution profile of a 120 mg capsule preparation of Diltiazem HCl in intestinal fluid according to USP 23 (Apparatus 1—baskets) according to an embodiment of the invention.

Figure 7:
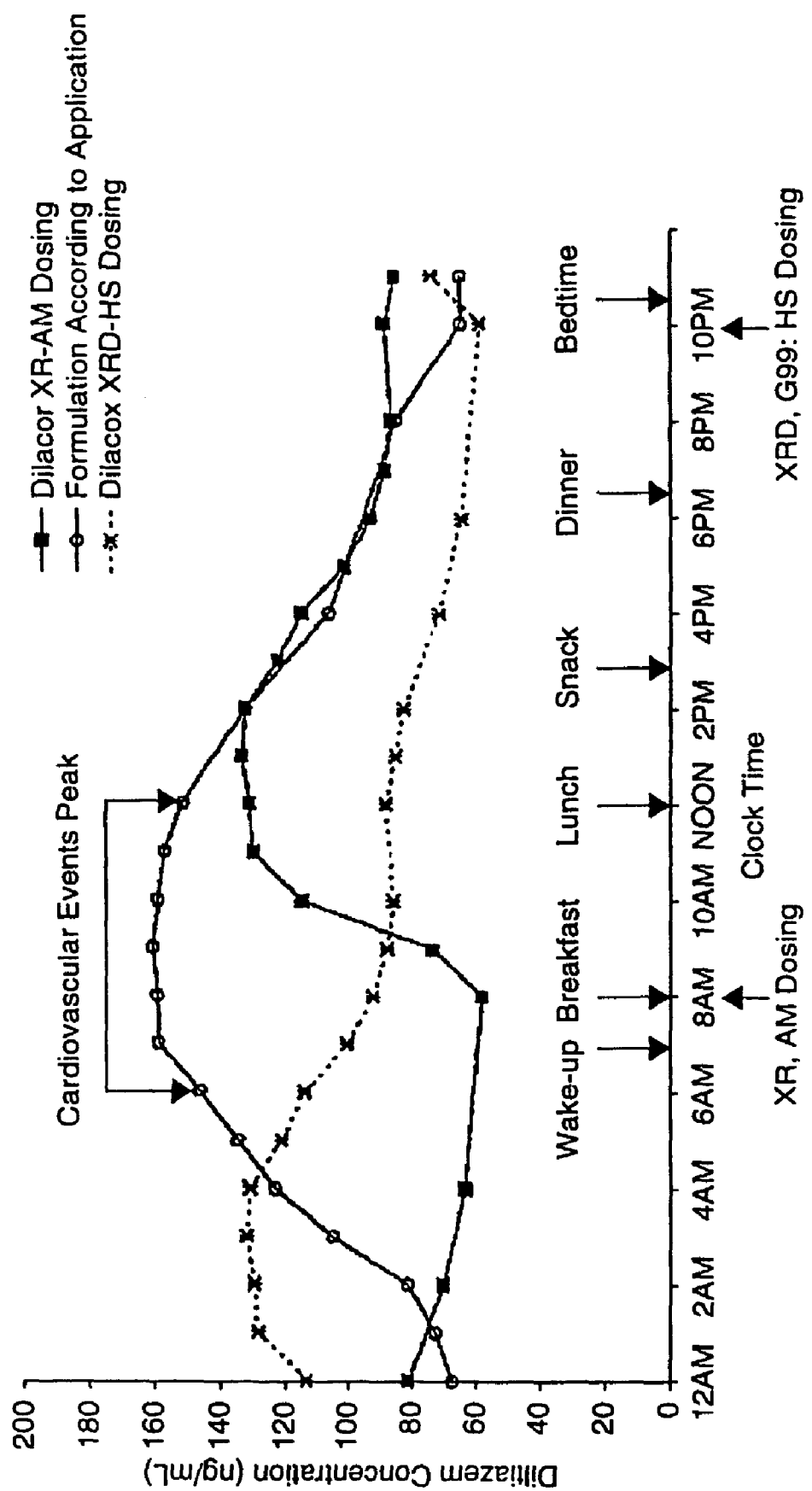

FIG. 7: is a graphic comparison of the blood level concentrations of a preparation (240 mg) made according to an embodiment of the invention and Dilacor (240 mg), a 24-hour oral sustained release dosage form of Diltiazem.

Figure 8:
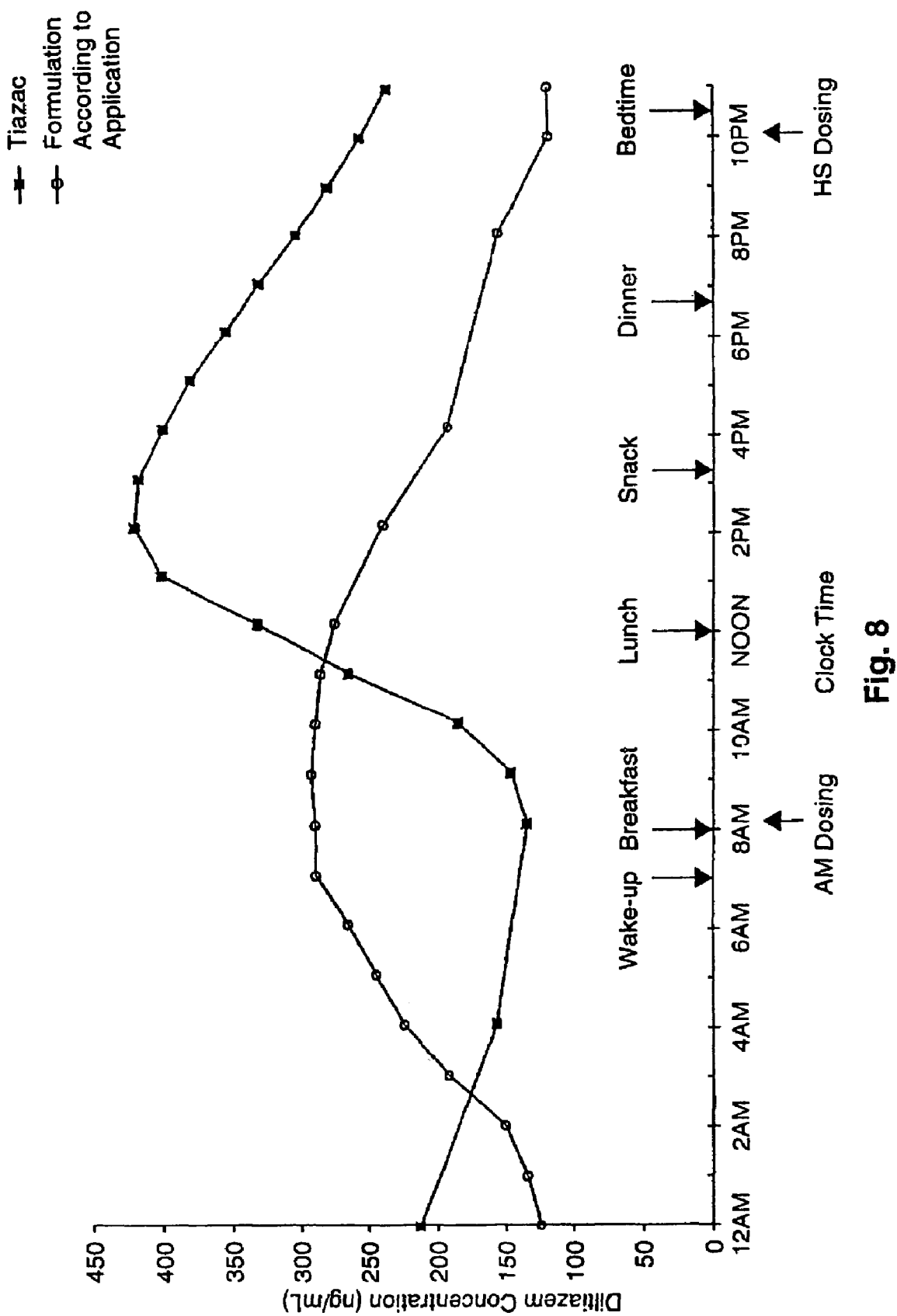

FIG. 8: is a graphic comparison of the blood level concentrations of a preparation (240 mg) made according to an embodiment of the invention and Tiazac (240 mg), a 24-hour oral sustained-release dosage form of Diltiazem.

Figure 9:
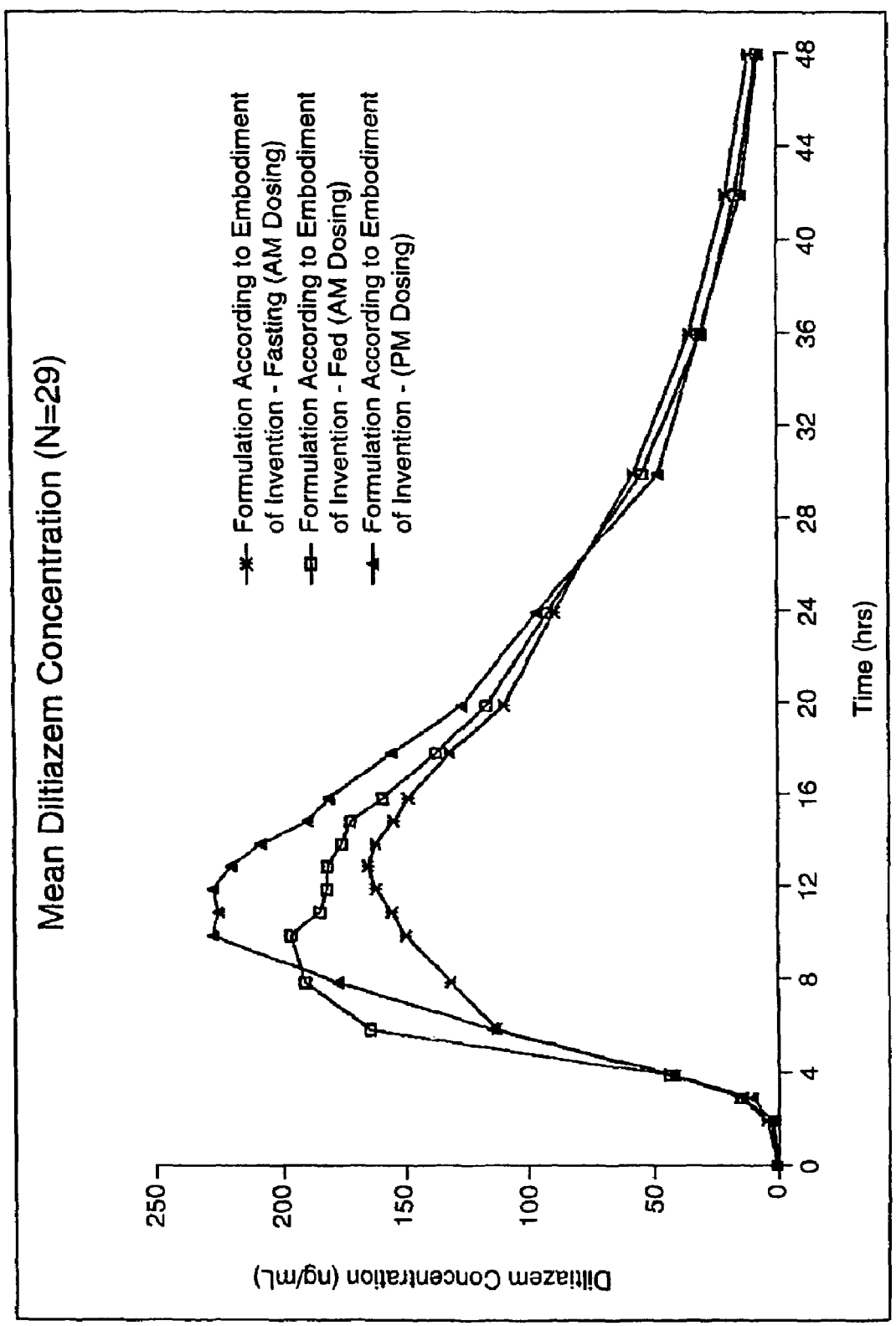

FIG. 9: illustrates graphically the Mean Diltiazem Concentration when administration of the same dosage form, is given in the P.M., in the A.M. with food and in the A.M. with fasting (without food) by 29 persons.

Figure 10:
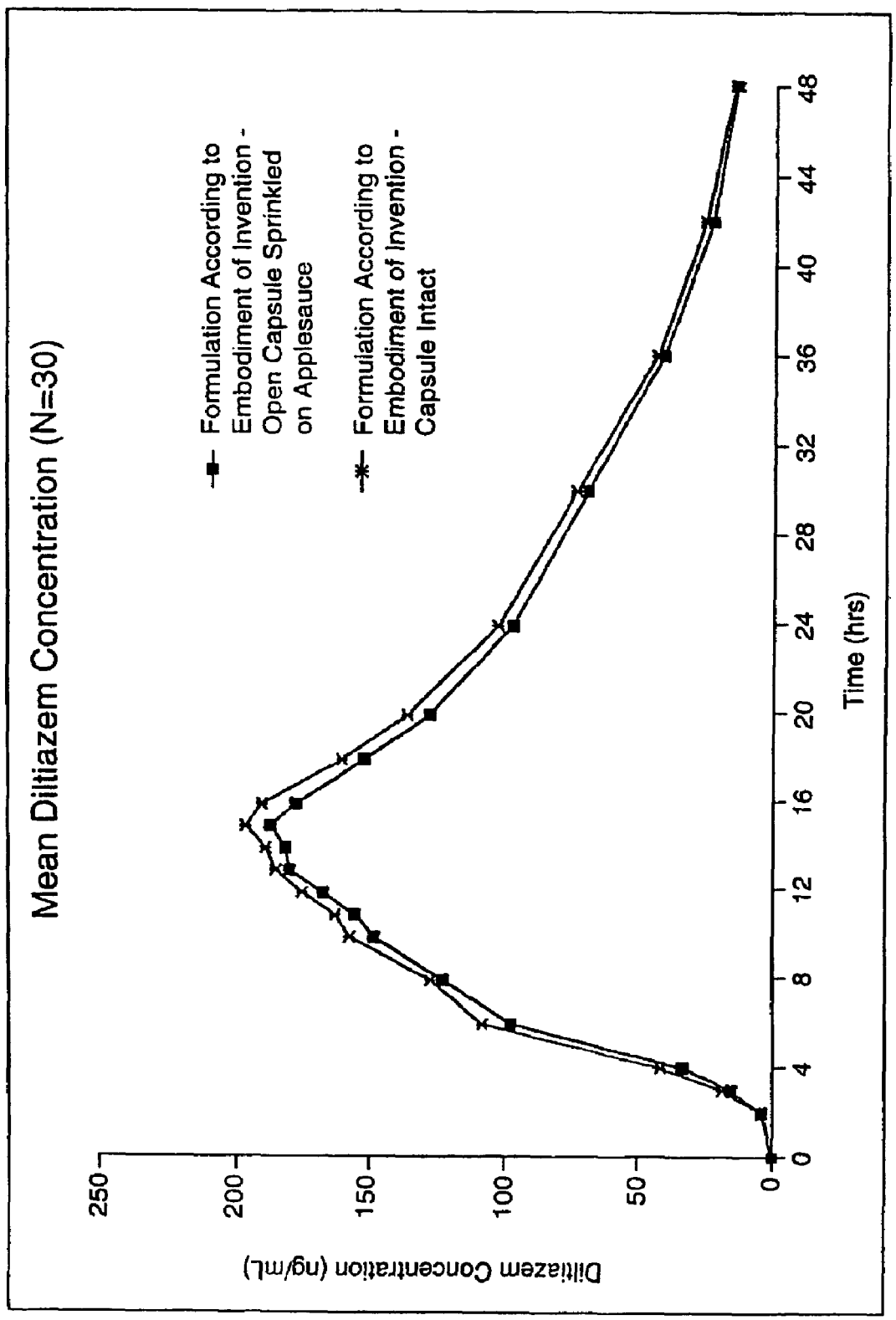

FIG. 10: illustrates graphically the Mean Diltiazem Concentration when the dosage form is an open capsule sprinkled on applesauce and swallowed and the dosage form is swallowed intact by 30 persons.

Figure 11:
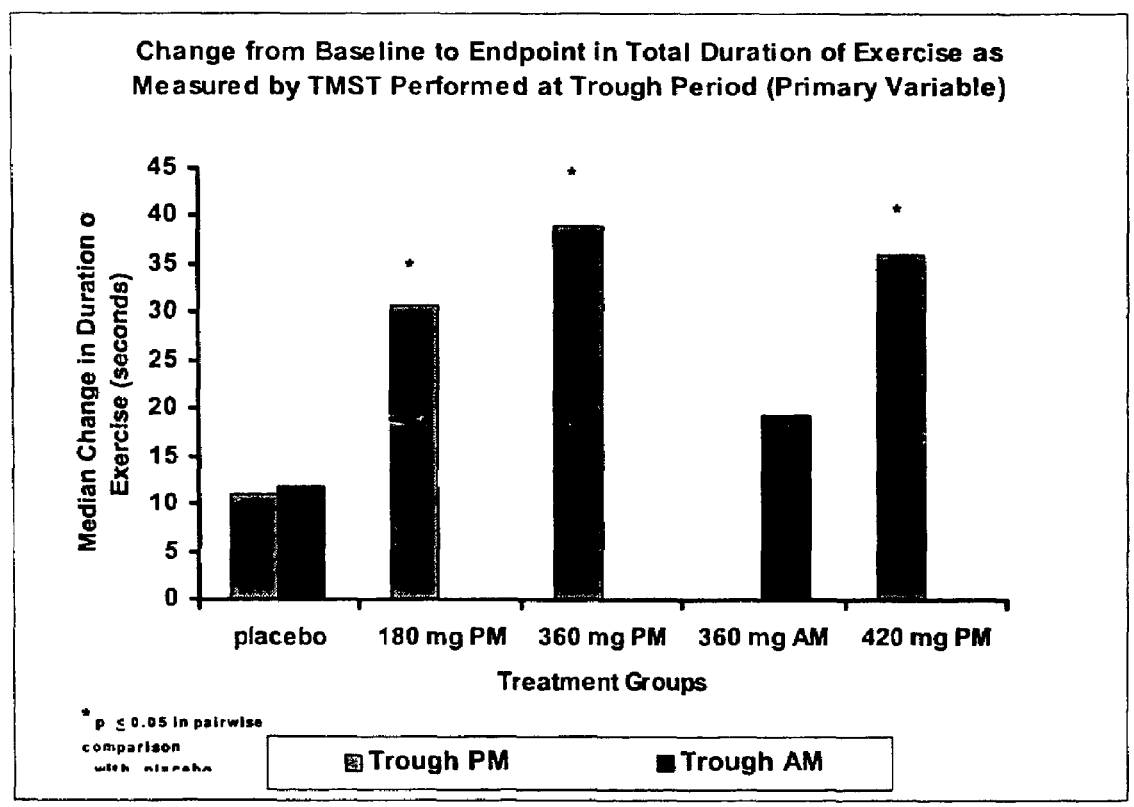

FIG. 11: illustrates the change from baseline to endpoint in total duration of exercise as measured by treadmill stress test performed at through period (primary variable).

Figure 12:
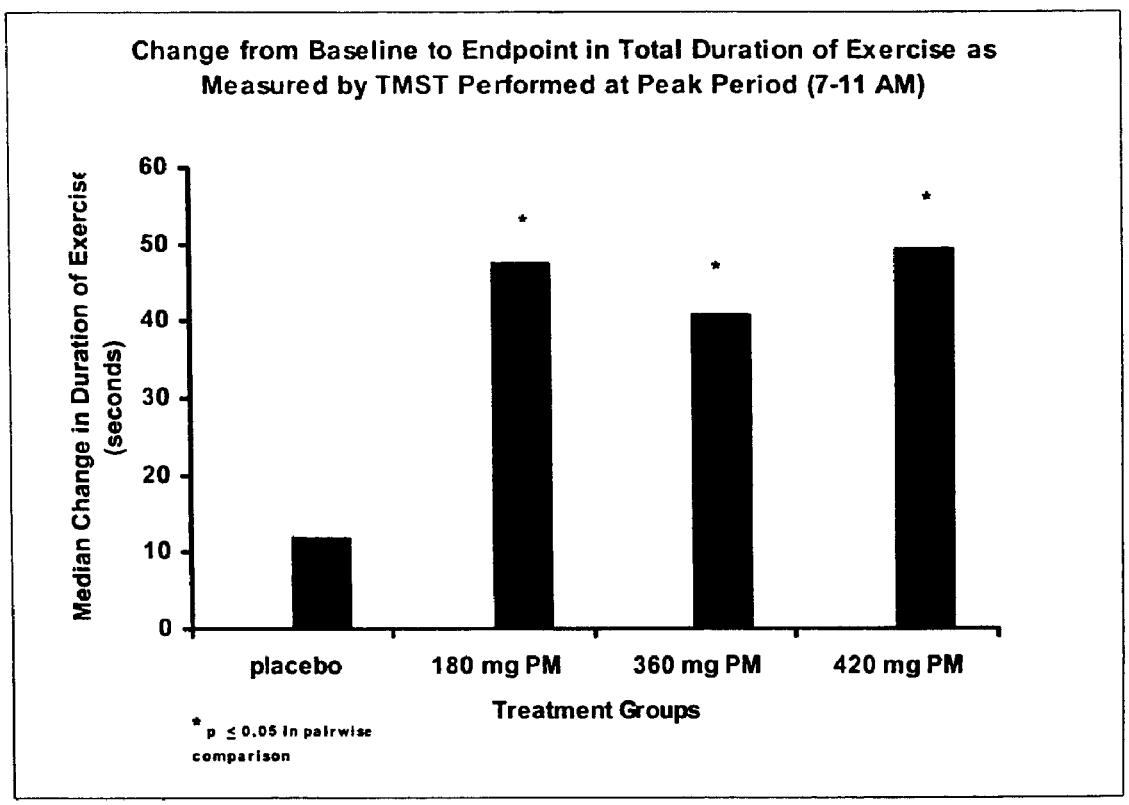

FIG. 12: illustrates the change from baseline to endpoint in total duration of exercise as measured by treadmill stress test performed at peak period (7-11 a.m.).

Figure 13:
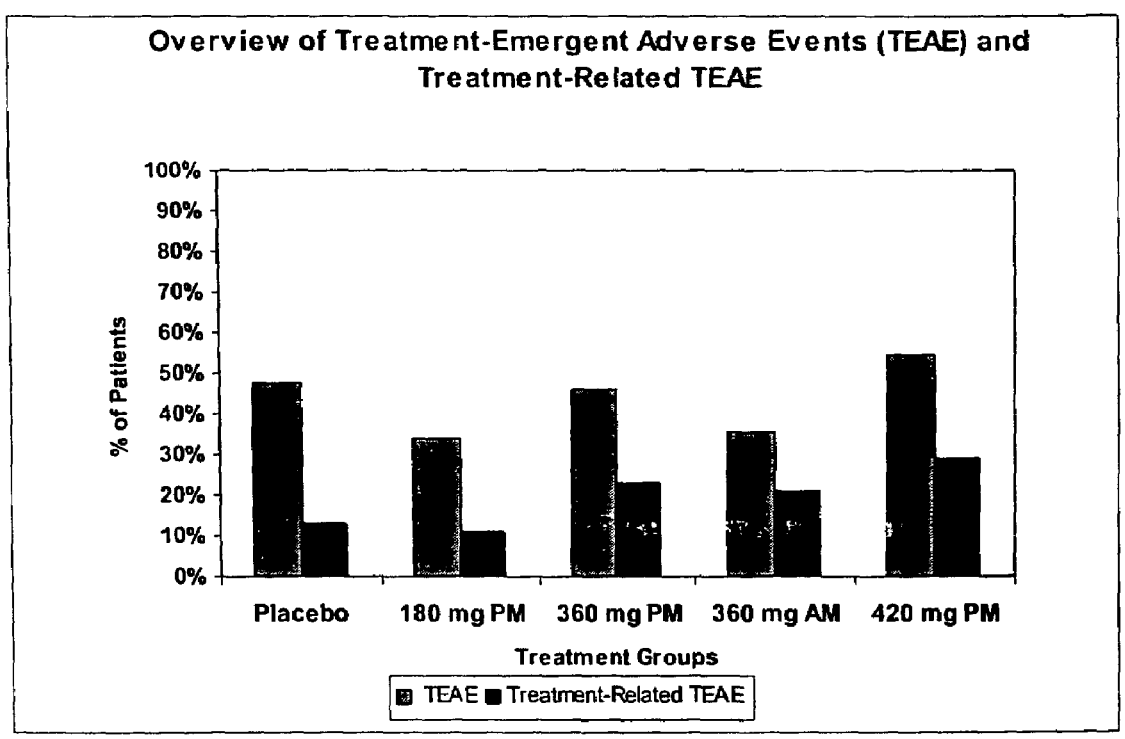

FIG. 13: illustrates the treatment-emergent adverse events (TEAE) and treatment-related TEAE.

Preparations were manufactured according to the percentages and constituents set out below:

| Component | % W/W |
|---|---|
| (1) Diltiazem hydrochloride | 69-73 |
| (2) Microcrystalline cellulose (Avicel ph101) | 8-9.5 |
| (3) Povidone K30 | 1-2 |
| (4) Sucrose stearate (crodesta F150) | 7-8 |
| (5) Magnesium stearate NF | 0.5-2.5 |
| (6) Talc USP | 0.5-5.0 |
| (7) Titanium dioxide (USP) | 0.15-0.3 |
| (8) Hydroxypropylmethylcellulose 2910 | 0.3-0.6 |
| (9) Polysorbate 80 (tween) | 0.01-0.025 |
| (10) Simeticone C emulsion USP (dry of 30%) | 0.01-0.015 |
| (11) Eudragit NE30 D (dry of 30%) | 7-11 |
| (12) Purified water USP | 0 |

Two Examples of preparations given the above percentages were made as 120 mg and 180 mg strengths of Diltiazem (as the HCl salt) in capsule form.

| Example 2 Strength 120 mg capsule | Example 3 Strength 180 mg capsule |
|---|---|
| (1) 120.00 | (1) 180.00 |
| (2) 13.63-16.18 | (2) 20.44-24.27 |
| (3) 1.7-3.41 | (3) 2.56-5.11 |
| (4) 11.92-13.63 | (4) 17.88-20.44 |
| (5) 0.852-4.26 | (5) 1.278-6.388 |
| (6) 0.852-8.52 | (6) 1.278-12.78 |
| (7) 0.256-0.511 | (7) 0.383-0.767 |
| (8) 0.511-1.02 | (8) 0.7665-1.533 |
| (9) 0.0170-0.0426 | (9) 0.0256-0.0639 |
| (10) 0.017-0.0256 | (10) 0.0255-0.383 |
| (11) 11.92-18.74 | (11) 17.886-28.106 |
| (12) 0 | (12) 0 |

240 mg, 300 mg, 360 mg and 420 mg strength preparations in capsule form of Diltiazem (as the HCl salt) were also prepared having the same percentages. They provide the release patterns shown in FIG. 3. The dissolution profiles of all of the strengths were generated from biobatches of capsules using Apparatus 1 (baskets) at 100 RPM in 900 ml of water in accordance with USP 23.

Less than 20% of the formulation is dissolved after about four hours (for example between about 16%-21%) with less than about 10% dissolved in the first two hours (for example between about 4%-about 8%). Less than about 50% is released after 8 hours (for example between about 44%-52%). Less than about 73% is released after 14 hours (for example 69%-76%). Preferably in excess of about 85% is released after 24 hours.

Specifically, samples of 120 mg capsules of Diltiazem HCl (made according to the embodiment of the invention) had the following dissolution profile:

| Percent Dissolved - Time Elapsed | | | | | | | | | |
|---|---|---|---|---|---|---|---|---|---|
| 2 h (%) | | 4 h (%) | | 8 h (%) | | 14 h (%) | | 24 h (%) | |
| 5 | 8 | 19 | 19 | 49 | 49 | 72 | 72 | 88 | 88 |
| 4 | 5 | 16 | 14 | 32 | 44 | 76 | 69 | 93 | 86 |
| 5 | 6 | 18 | 16 | 50 | 49 | 72 | 73 | 88 | 90 |
| 7 | 6 | 21 | 17 | 54 | 48 | 76 | 72 | 92 | 87 |
| 5 | 8 | 17 | 19 | 51 | 50 | 74 | 74 | 92 | 91 |
| 6 | 7 | 18 | 19 | 52 | 52 | 74 | 75 | 90 | 92 |
| Mean (%) 6 | | 18 | | 50 | | 73 | | 90 | |
| RSD 21.3 | | 10.5 | | 5.1 | | 2.7 | | 2.6 | |

Samples of 180 mg capsules of Diltiazem HCl (made according to an embodiment of the invention) had the following dissolution profiles:

| Lapsed Time | Percent Dissolved - Time Elapsed | | | | | | | | |
|---|---|---|---|---|---|---|---|---|---|
| | 2 h (%) | | 4 h (%) | | 8 h (%) | | 14 h (%) | | 24 h (%) | |
| | 8 | 7 | 21 | 20 | 52 | 52 | 76 | 73 | 91 | 89 |
| | 6 | 7 | 19 | 20 | 52 | 51 | 76 | 73 | 93 | 90 |
| | 5 | 6 | 16 | 18 | 48 | 50 | 72 | 72 | 89 | 90 |
| | 6 | 7 | 19 | 18 | 52 | 49 | 76 | 72 | 98 | 88 |
| | 7 | 7 | 20 | 19 | 51 | 51 | 73 | 74 | 91 | 91 |
| | 8 | 7 | 20 | 21 | 51 | 51 | 74 | 73 | 92 | 91 |
| Mean (%) | 7 | | 19 | | 51 | | 74 | | 91 | |
| RSD | 12.8 | | 7.4 | | 2.5 | | 2.1 | | 1.7 | |

Samples of 240 mg capsules of Diltiazem HCl (made according to an the invention) had the following dissolution profiles:

| Percent Dissolved - Time Elapsed | | | | | | | | | |
|---|---|---|---|---|---|---|---|---|---|
| 2 h (%) | | 4 h (%) | | 8 h (%) | | 14 h (%) | | 24 h (%) | |
| 6 | 4 | 19 | 16 | 46 | 48 | 73 | 71 | 86 | 86 |
| 6 | 5 | 18 | 15 | 48 | 45 | 70 | 68 | 85 | 84 |
| 5 | 5 | 18 | 17 | 49 | 49 | 71 | 72 | 86 | 88 |
| 4 | 7 | 16 | 18 | 46 | 48 | 68 | 71 | 83 | 87 |
| 6 | 4 | 18 | 15 | 49 | 50 | 70 | 68 | 84 | 84 |
| 6 | 6 | 18 | 17 | 48 | 48 | 70 | 71 | 85 | 86 |
| Mean (%) | 5 | | 17 | | 48 | | 70 | | 85 |
| RSD | 18.5 | | 7.7 | | 2.9 | | 2.3 | | 1.7 |

Samples of Diltiazem HCl capsules 300 mg (made according to an embodiment of the invention) had the following dissolution profile:

| Percent Dissolved - Time Elapsed | | | | | | | | | |
|---|---|---|---|---|---|---|---|---|---|
| 2 h (%) | | 4 h (%) | | 8 h (%) | | 14 h (%) | | 24 h (%) | |
| 3 | 4 | 16 | 16 | 46 | 45 | 68 | 67 | 83 | 83 |
| 6 | 5 | 17 | 16 | 49 | 45 | 73 | 67 | 90 | 83 |
| 6 | 5 | 16 | 16 | 46 | 46 | 69 | 68 | 84 | 84 |
| 5 | 5 | 16 | 16 | 46 | 46 | 69 | 69 | 83 | 87 |
| 6 | 4 | 17 | 15 | 46 | 45 | 68 | 68 | 82 | 86 |
| 5 | 5 | 17 | 17 | 46 | 47 | 69 | 70 | 84 | 87 |
| Mean (%) | 5 | | 16 | | 46 | | 69 | | 85 |
| RSD | 13.2 | | 3.8 | | 2.4 | | 2.3 | | 2.8 |

Additionally, the following Dissolution Profiles were obtained for the samples of 120 mg Diltiazem HCl Capsules:

Medium: Water

| Hour | Diltiazem HCl Capsules % Dissolved (Average of 12 capsules) | Range [%] | RSD |
|---|---|---|---|
| 2 | 6 | 4-8 | 17.6 |
| 4 | 18 | 14-21 | 9.8 |
| 8 | 50 | 44-54 | 5.1 |
| 14 | 73 | 69-76 | 2.8 |
| 24 | 90 | 86-93 | 2.5 |

Medium: Gastric Fluid

| Hour | Diltiazem HCl Capsules % Dissolved (Average of 12 capsules) | Range [%] | RSD |
|---|---|---|---|
| 2 | 5 | 3-6 | 18.8 |
| 4 | 16 | 14-18 | 9.0 |
| 8 | 49 | 47-52 | 3.5 |
| 14 | 73 | 71-75 | 1.8 |
| 24 | 87 | 85-89 | 1.5 |

Medium: Intestinal Fluid

| Hour | Diltiazem HCl Capsules % Dissolved (Average of 12 capsules) | Range [%] | RSD |
|---|---|---|---|
| 2 | 5 | 3-7 | 26.0 |
| 4 | 17 | 14-20 | 12.0 |
| 8 | 43 | 40-47 | 6.1 |
| 14 | 64 | 53-69 | 8.1 |
| 24 | 78 | 65-85 | 8.1 |

Other Dissolution Profiles were Determined of Embodiments of the Invention (Medium - USP Water)
Apparatus: USP #1 (baskets) at 100 rpm
Diltiazem 120 mg Capsules

| | TIME [h] | | | | |
|---|---|---|---|---|---|
| | 2 | 4 | 8 | 14 | 24 |
| vessel 1 | 5% | 19 | 49 | 72 | 88 |
| vessel 2 | 4 | 16 | 52 | 76 | 93 |
| vessel 3 | 5 | 18 | 50 | 72 | 88 |
| vessel 4 | 7 | 21 | 54 | 76 | 92 |
| vessel 5 | 5 | 17 | 51 | 74 | 92 |
| vessel 6 | 6 | 18 | 52 | 74 | 90 |
| vessel 7 | 8 | 19 | 49 | 72 | 88 |
| vessel 8 | | 14 | 44 | 69 | 86 |
| vessel 9 | | 16 | 49 | 73 | 90 |
| vessel 10 | 6 | 17 | 48 | 72 | 87 |
| vessel 11 | 8 | 19 | 50 | 74 | 91 |
| vessel 12 | 7 | 19 | 52 | 75 | 92 |
| MEAN | 6% | 18 | 50 | 73 | 90 |
| SD | 1.3 | 1.9 | 2.6 | 2.0 | 2.3 |
| RSD | 21.3 | 10.5 | 5.1 | 2.7 | 2.6 |
| RANGE | 4-8 | 14-21 | 44-54 | 69-76 | 86-93 |

(Medium - Gastric)
Apparatus: USP #1 (baskets) at 100 rpm
Diltiazem 120 mg Capsules

| | TIME [h] | | | | |
|---|---|---|---|---|---|
| | 2 | 4 | 8 | 14 | 24 |
| vessel 1 | 3 | 14 | 51 | 74 | 88 |
| vessel 2 | 6 | 17 | 48 | 72 | 85 |
| vessel 3 | 5 | 17 | 49 | 72 | 85 |
| vessel 4 | 5 | 15 | 48 | 72 | 87 |
| vessel 5 | 4 | | 47 | 71 | 86 |
| vessel 6 | 6 | 18 | 50 | 72 | 86 |
| vessel 7 | | 15 | 49 | 73 | 88 |
| vessel 8 | 4 | 14 | 48 | 71 | 86 |
| vessel 9 | 5 | 17 | 51 | 74 | 88 |
| vessel 10 | 6 | 18 | 52 | 74 | 88 |
| vessel 11 | 6 | 18 | | 75 | 89 |
| vessel 12 | 5 | 17 | 50 | 73 | 87 |
| MEAN | 5 | 16 | 49 | 73 | 87 |
| SD | 0.9 | 1.5 | 1.7 | 1.3 | 1.3 |
| RSD | 19.0 | 9.0 | 3.5 | 1.8 | 1.5 |
| RANGE | 3-6 | 14-18 | 47-52 | 71-75 | 85-89 |

(Medium - Intestinal)
Apparatus: USP #1 (baskets) at 100 rpm
Diltiazem 120 mg Capsules

| | TIME [h] | | | | |
|---|---|---|---|---|---|
| | 2 | 4 | 8 | 14 | 24 |
| vessel 1 | 7 | 19 | 45 | 67 | 81 |
| vessel 2 | 4 | 14 | 40 | 64 | 79 |
| vessel 3 | 7 | 20 | 47 | 69 | 83 |
| vessel 4 | 5 | 19 | 46 | 68 | 83 |
| vessel 5 | | 17 | 41 | 58 | 69 |
| vessel 6 | | 17 | 45 | 69 | 83 |
| vessel 7 | 4 | 17 | 40 | 53 | 65 |
| vessel 8 | 5 | 17 | 42 | 65 | 78 |
| vessel 9 | 5 | | | 58 | 73 |
| vessel 10 | 5 | 17 | 47 | 68 | 85 |
| vessel 11 | 4 | 15 | 44 | 64 | 81 |
| vessel 12 | 4 | 15 | 43 | 64 | 81 |
| MEAN | 5 | 17 | 43 | 64 | 78 |
| SD | 1.2 | 2.0 | 2.7 | 5.2 | 6.4 |
| RSD | 25.9 | 13.0 | 6.1 | 8.1 | 8.1 |
| RANGE | 3-7 | 14-20 | 40-47 | 53-69 | 65-85 |

Briefly, the dosages in Examples 1 (120 mg) and 2 (180 mg), the 240 mg, 300 mg, 360 mg and 420 mg dosages were manufactured by mixing the core (bead) ingredients (diltiazem, microcrystalline cellulose, povidone, sucrose stearate) by introducing the components into a planetary mixer and granulating same and mixing with purified water. The plastic mass was then extruded to provide an extrudate. The extrudate was subsequently spheronized to produce diltiazem spheres in admixture with the wetting agent. The spheres (cores) were dried in an oven and sieved to the appropriate size cores or beads.

The membrane was prepared by mixing the hydroxypropylmethylcellulose, titanium dioxide, talc, magnesium stearate, Polysorbate 80 and Simethacone C emulsion and thereafter combined with the Eudragit NE30D and water. The spheronized cores were coated with the appropriate thickness of membrane by spraying the cores, coating same. Thus the cores (beads) were coated with the coating suspension to produce the microgranules or pellets. The microgranules or pellets were then dried.

In more detail, the process combines Diltiazem Hydrochloride USP, Microcrystalline cellulose NF (Avicel PH 101), Povidone K30 USP and Sucrose Stearate (Crodesta F160) as follows: The following were screened through a 1.9 mm screen and added to a mixer bowl:
Diltiazem
Avicel PH 101
Povidone K30.

To remove large agglomerates, the Crodesta 7.98 kg was screened through a 1.0-1.2 mm screen and added to the same mixing bowl. The items were then blended in an AMF blender at 50 RPM. 1 kg of the above dry blend was set aside to be used as dusting powder (Diltiazem Dusting Powder). The remainder of the blend was continued to be blended at 50 rpm until adequately granulated. The granulated material was then loaded into the hopper of an extruder (such as EXDCS100 or EXDS 60). The granulation was extruded and without breaking up the extrudate, the extrudate was collected. The extrudate was then spheronized into the cores (beads) of the desired size and were dusted as desired by the Diltiazem Dusting Powder set aside. The beads were then dried by spreading them on trays and drying in an oven set at about 57° C. The Drying Temp. was in the order of 55-60° C. for about 12 hours (in the order of 12-16 hours). The dried cores (beads) were sieved to collect those of appropriate size (0.7-1.4 mm).

A Eudragit NE30D and hydroxypropylmethylcellulose coating suspension, was made. The following:
Magnesium Stearate NF
Talc USP
Titanium Dioxide USP
Hydroxypropylmethylcellulose 2910 USP (Pharmacoat 606)
Polysorbate 80 NF (Tween 80)
Simethicone C Emulsion USP and pure water were combined within a Silverson Mixer. Water was first mixed with Polysorbate 80 and the Simethicone. The HPMC was then added, then titanium dioxide, then talc and then the Magnesium Stearate. The mixture was stored for 2 hours. The Eudragit NE30D was screened through a 0.310 mm sieve and added to the mixture.

The beads were then coated with the suspension by using an Aerocoater™ and spraying the beads (which have been preheated to 26° C.) with the coating suspension to achieve the desired thickness (about 0.05 mm). The beads were then dried by spreading on trays and drying at 40-45° C. for 10-12 hours.

Diltiazem HCl 300 mg capsules made according to an embodiment of the invention were tested in a single dose study to determine their bioavailability, their Cmax and Tmax, their rate and extent of absorption.

Blood sampling for drug content analysis was carried out at 0.0 (predrug) 1, 2, 3, 4, 5, 6, 8, 10, 12, 14, 16, 18, 24, 30, 36, 42 and 48 hours post-drug. Vital sign and 12-Lead ECG monitoring were conducted at 0 (predrug) 2, 6, 8 and 12 hours post-drug. The following was determined from the plasma study:

| Mean Pharmacokinetic Parameters for Plasma Diltiazem (n = 41) | |
|---|---|
| Parameter | 1 × 300 mg Mean (% CV) |
| AUC (0-t)(ng · hr/mL) | 2703.83 (36.26) |
| AUC (0-inf.)(ng · hr/mL) | 2786.95 (36.39) |
| $C_{max}$ (ng/mL) | 146.33 (38.43) |
| $T_{max}$ (hours) | 13.17 (14.79) |
| $t_{1/2}$ (hours) | 6.96 (17.56) |
| $K_{el}$ (hour$^{-1}$) | 0.102 (15.983) |

| Mean Plasma Diltiazem Concentrations (ng/mL) (n = 41) | |
|---|---|
| SAMPLE TIME (HOURS) | 1 × 300 mg |
| 0.00 | 0.00 ± 0.00 |
| 1.00 | 0.76 ± 2.20 |
| 2.00 | 4.92 ± 3.87 |
| 3.00 | 10.97 ± 5.92 |
| 4.00 | 20.01 ± 10.77 |
| 5.00 | 33.46 ± 18.39 |
| 6.00 | 70.21 ± 37.03 |
| 8.00 | 95.43 ± 41.50 |
| 10.00 | 110.16 ± 47.43 |
| 12.00 | 132.84 ± 52.04 |
| 14.00 | 139.54 ± 55.11 |
| 16.00 | 126.35 ± 50.23 |

-continued

Mean Plasma Diltiazem Concentrations (ng/mL)
(n = 41)

| SAMPLE TIME (HOURS) | 1 × 300 mg |
|---|---|
| 18.00 | 105.74 ± 40.86 |
| 24.00 | 62.84 ± 24.20 |
| 30.00 | 43.92 ± 16.94 |
| 36.00 | 25.67 ± 11.46 |
| 42.00 | 13.40 ± 7.37 |
| 48.00 | 7.50 ± 4.46 |

Mean Pharmacokinetic Parameters for Plasma Diltiazem
(n = 36)

| Parameter | Geometric Mean<br>Arithmetic Mean (C.V.)<br>1 × 300 mg |
|---|---|
| AUC (0-t hours)(ng · hr/mL) | 2682.87 |
| | 2872.06 (38.44) |
| AUC (0-x)(ng · hr/mL) | 1955.92 |
| | 2075.00 (35.63) |
| AUC (0-infinity)(ng · hr/mL) | 2847.57 |
| | 3055.19 (39.05) |
| $C_{max}$ (ng/mL) | 134.96 |
| | 144.00 (37.17) |
| $T_{max}$ (hours)** | 13.00 (2.92) |
| $t_{1/2}$ (hours)* | 8.69 (22.85) |
| $K_{el}$ (hour$^{-1}$)* | 0.084 (22.860) |

*These are arithmetic means (CV %).
**This is median (±S.D.).

With reference to FIGS. 1 and 2, it is clear the 300 mg capsule preparation made according to an embodiment of the invention provides the appropriate Diltiazem blood levels at the appropriate time to be suitable for administration as a chronotherapeutic—being given in the evening to provide effective concentrations of Diltiazem the following morning. This suitability is illustrated with reference to FIGS. 7 and 8. In FIG. 7, the 240 mg Diltiazem preparation made according to the embodiment of the invention provides elevated blood levels that are effective all morning for effective treatment of the patient with Diltiazem. However, the Dilacor formulation (given either in the evening or the following morning) does not protect the patient from 6:00 a.m.-noon, the more dangerous period.

The same is true with FIG. 8. Tiazac given in the morning, does not provide the protection. Further, peak plasma concentrations for Tiazac are achieved after about 7 hours after dose administration.

A 3-way single-dose study was undertaken using the same formulation (420 mg capsule) administered in the P.M. (10:00 P.M.) without food, and in the A.M. dosing with and without food.

3-Way Single-Dose Study

A: Formulation According to Embodiment of Invention—Fasting (AM Dosing)

B: Formulation According to Embodiment of Invention—Fed (AM Dosing)

C: Formulation According to Embodiment of Invention—(PM Dosing) N=29

The results illustrated in FIGS. 9A and FIG. 9B were found whose mean were graphically illustrated in FIG. 9.

A 2-way single-dose fasting study was undertaken using the same formulation (420 mg capsule) administered in the following manners—capsule intact and capsule opened and sprinkled on applesauce and ingested.

2-Way Single Dose Fasting Study

A: Formulation According to Embodiment of Inventions—Open Capsule Sprinkled on Applesauce B: Formulation According to Embodiment of Inventions—Capsule Intact N=30 (FINAL DATA)

The results illustrated in FIGS. 10A, 10B and 10C were found whose mean were graphically illustrated in FIG. 10.

The preparations according to embodiments may also be made as tablets. The tablets may be made as compressed tablets in the desired strengths (for example 120 mg-540 mg or more Diltiazem) incorporating the microgranules. The tablets may even be scored to permit division into smaller doses.

Tablets may be made as follows using the microgranules or pellets, wax placebo beads and hydrogenated vegetable oil, sodium starch glycolate and silicone dioxide as follows:

The microgranules of Diltiazem may be the following:
Magnesium Stearate
Talc
Titanium Dioxide
Hydroxypropylmethyl-Cellulose 2910
Polysorbate 80
Simethicone Emulsion
Eudragit NE30D
Diltiazem Hydrochloride
Microcrystalline Cellulose
Povidone K30
Sucrose Stearate
Purified Water The wax placebo beads may be the following:
Microcrystalline Wax NF
Pregelatinized Starch
Sodium Starch Glycolate
Titanium Dioxide
Carbon Dioxide The microgranules, wax placebo beads, hydrogenated vegetable oil, sodium starch glycolate and silicone dioxide may be combined and compressed into the desired strengths of tablets, for example 240 mg, 300 mg and 360 mg tablets.

Briefly, to form the microgranules, Diltiazem HCl, Microcrystalline Cellulose, Povidone 30, Sucrose Stearate may be mixed to form a "dry blend". A 1 kg portion of the dry blend may be removed and stored in a separate labeled container as the Dusting Powder, for use in subsequent manufacturing steps (if desired). Following the removal of the Dusting Powder, Purified Water is added to the dry blend and mixed to create a plastic mass. The plastic mass is extruded through a 1.0 mm screen to form a spaghetti like extrudate. This extrudate is then spheronized into beads. During the spheronization process Dusting Powder is added to dry the beads and provide them with a smooth aspect (if required). The addition of Dusting Powder also prevents the newly spheronized beads from sticking together. The spheronized beads are tray dried for 12-16 hours and sieved to select beads that are larger than 0.7 mm and smaller than 1.4 mm in diameter.

The beads are loaded into a preheated (40-45° C.) fluid bed Aerocoater. Coating suspension is applied at an amount of 10% by spray coating. The resulting Diltiazem Microgranules (coated beads) are dried for between 10-12 hours and the dried coated beads are sieved to select coated beads that are larger than 0.7 mm and smaller than 1.7 mm in diameter.

For the manufacture of the placebo wax beads, Microcrystalline Wax, Pregelatinized Maize Starch, Sodium Starch Glycolate and Titanium Dioxide are mixed in a high shear mixer and heated to 64° C. (jacket temperature 70° C.). The resulting melt is cooled by the addition of liquid $CO_2$ to form the solid starters of the pellets. The pellet starters are mixed and the size is increased by the gradual turning of the impeller for a fixed timeperiod (mixing time is directly related to the impeller speed and the time to reach a temperature of 57±2° C.). The resulting beads are sieved to select beads larger than 0.7 mm and smaller than 1.4 mm in diameter.

For manufacturing the Diltiazem-chronotherapeutic tablets, the placebo wax beads and the microgranules of Diltiazem are blended at a ratio of about 2:3 (placebo wax beads: microgranules of Diltiazem) with Hydrogenated Vegetable Oil (lubricant), Sodium Starch Glycolate (disintegrant) and Silicone Dioxide (lubricant) added. The blend is tableted under low pressure (approximately 6-8 Sc) to form the compressed Diltiazem Tablets. In the compressed tablets, the placebo wax beads serve to absorb the shock placed on the microgranules of Diltiazem during the tableting process. By doing so the integrity of the microgranules remains in tact and the release rate of the diltiazem is not affected.

As many changes can be made to the embodiments of the invention without departing from the scope thereof, it is intended that all material contained herein be determined as illustrative of the invention and not in a limiting sense.

Referring now to FIGS. 11-13, a double blind, randomized, parallel-group, dose-response, multi-center study to assess the safety and efficacy of Diltiazem compared to placebo dosed at bedtime and to Diltiazem dosed in the morning in patients with chronic stable angina was conducted. A total of 311 patients>18 years of age were randomized to double-blind treatment.

The study design included a 2-to 3-week single blind, placebo run-in period, followed by a 1-week double-blind titration period, and a 2-week double-blind maintenance treatment period. After signing the informed consent form and meeting study inclusion/exclusion criteria at screening, patients discontinued any previously prescribed anti-angina medications with the exceptions of sublingual nitroglycerin (SL NTG) and stable doses of atenolol (limited to 50 mg/day or less). Once withdrawn from all excluded concomitant therapy and anti-angina agents for at least 24 hours, patients entered the single blind, placebo run-in period. Qualified patients were randomly assigned in a 1:1:1:1:1 ratio to placebo, Diltiazem 180 mg PM, 360 mg AM, 360 mg PM or 420 mg PM. Patients randomized to Diltiazem 360 mg AM, 360 mg PM and 420 mg PM were initially treated with Diltiazem 240 mg for 1 week and up titrated in a blinded fashion to their randomized treatment dose. Patients randomized to 180 mg did not require titration and remained on their starting dose throughout the double-blind treatment period. Following the 1-week titration period, all patients remained on maintenance treatment for 2 weeks. An evening treadmill stress test (TMST) was performed at 7 PM+1 hour after the first week and second week of the single blind, placebo run-in period (required for qualification) and was repeated at the end of the double-blind maintenance treatment phase. In addition, a morning TMST was performed at 9 AM+2 hours at the end of the single blind, placebo run-in period and at the end of the double-blind maintenance treatment period. Patients were evaluated for safety and efficacy weekly during the double-blind treatment.

The primary measure of efficacy was the change from baseline to final visit in total duration of exercise (in seconds) as measured by TMST performed during the Diltiazem trough period. The period of 6 PM to 8 PM was evaluated for 180 mg, 360 mg and 420 mg nighttime doses of Diltiazem and placebo while 7 AM to 11 AM was evaluated for Diltiazem 360 mg and placebo dosed in the morning. Total duration of exercise was defined as the total time the patient was able to exercise on the treadmill until the patient had to stop because of moderate angina (defined as the severity of pain that would ordinarily cause a patient to stop exercising during normal everyday activity).

There were 9 secondary variables that included change from baseline to final visit in total duration of exercise during 7 AM to 11 AM; change from baseline to final visit in time to onset of exercise-induced angina and time to onset of exercise-induced myocardial ischemia at trough and at 7 AM to 11 AM; the change from baseline to final visit in diastolic blood pressure (DBP), systolic blood pressure (SBP) and heart rate (HR); the change from baseline to final visit in rate pressure product (SBP×HR) at rest and during exercise; the frequency of angina attacks per week and the frequency of SL NTG consumption per week.

FIG. 11 summarizes the results of the analysis of the primary efficacy variable, median change from baseline to endpoint in total duration of exercise at trough (24 hours after dosing), for each nighttime dose of Diltiazem compared to placebo and for Diltiazem 360 mg dosed in the morning compared to placebo. A flat dose response was observed with all nighttime doses significantly different from placebo. Diltiazem 360 mg PM exhibited a somewhat greater response than either Diltiazem 180 mg PM or Diltiazem 420 mg PM. The Diltiazem 360 mg morning dose was borderline not significantly different from placebo ($p=0.0555$). About a 2-fold greater improvement in exercise performance was demonstrated for Diltiazem 360 mg PM at trough compared to Diltiazem 360 mg AM at trough.

The results of the intent-to-treat analysis of the secondary efficacy variable, median change from baseline to endpoint in total duration of exercise for nighttime doses of Diltiazem compared to placebo during 7 AM to 11 AM (the period of the day when the incidence of cardiovascular events is highest and angina attacks is greatest) are shown in FIG. 2. All nighttime doses were statistically significantly different from placebo. A flat dose response was observed with the Diltiazem 420 mg PM dose somewhat better than either the Diltiazem 180 mg PM or Diltiazem 360 mg PM doses. Additional improvement in exercise performance was demonstrated during 7 AM to 11 AM coinciding with the highest plasma levels of Diltiazem AM compared to the 6 PM to 8 PM time period that coincides with the period of the lowest plasma levels of Diltiazem (Table 1).

TABLE 1

Comparison of Median Change from Baseline to Endpoint for Total Duration of Exercise 6 PM to 8 PM v. 7 AM to 11 AM Nighttime Doses of Diltiazem

| Dose | 6 PM to 8 PM | 7 AM to 11 AM | AM/PM Ratio |
| --- | --- | --- | --- |
| 180 mg | 30.8 | 47.5 | 1.5 |
| 360 mg | 39.0 | 41.0 | 1.1 |
| 420 mg | 36.0 | 49.5 | 1.4 |

A post-hoc analysis was performed to evaluate the efficacy of Diltiazem 360 mg AM based upon total duration of exercise measured by TMST during its maximum plasma levels (6 PM to 8 PM). As shown in Table 2, a statistically significant difference from placebo in median change from baseline to endpoint favoring Diltiazem was observed. Efficacy of Diltiazem 360 mg AM at its peak was comparable to Diltiazem 360 mg PM at its peak. However, as shown previously, Diltiazem 360 mg PM was superior to Diltiazem 360 mg AM at trough.

TABLE 2

Post-Hoc Comparison of Diltiazem 360 mg PM and Diltiazem 360 mg AM
Median Change from Baseline to Endpoint in Total Duration of Exercise
(ITT Population)

|  | Peak | | Trough | |
| --- | --- | --- | --- | --- |
|  | 360 PM (7 AM-11 AM) | 360 AM (6 PM-8 PM) | 360 PM (6 PM-8 PM) | 360 AM (7 AM-11 AM) |
| Median Change (sec) | 41.0 | 40.0 | 39.0 | 19.5 |
| p-value vs. placebo | 0.0002 | 0.0118 | 0.0087 | 0.0555 |

Table 3 summarizes the results of the intent-to-treat analysis of two additional secondary variables, time to onset of angina and time to onset of myocardial ischemia (ST segment depression) as measured by TMST performed at 6 PM-8 PM and at 7 AM-11 AM. Table 4 compares efficacy for nighttime dosing for the two time intervals. Each variable was evaluated in two ways. The first analysis was the median change from baseline to endpoint for those patients who experienced angina and myocardial ischemia (Dunnett's procedure). The second analysis was undertaken because when on active drug, greater than 20% of the patients in several treatment groups were censored (i.e., did not exhibit angina and/or myocardial ischemia). Accordingly, a survival analysis using the Kaplan-Meier procedure to estimate the median time to onset (of angina and myocardial ischemia) at the final visit was undertaken.

TABLE 4

Comparison of Peak (7 AM to 11 AM) vs.
Trough (6 PM to 8 PM) Efficacy for Secondary
Variables Following Nighttime Doses of
Diltiazem (ITT Population)

| Dose | Onset of Angina | | Onset of Myocardial Ischemia | |
| --- | --- | --- | --- | --- |
|  | Dunnett's | Kaplan-Meier | Dunnett's | Kaplan-Meier |
| DILTIAZEM 180 PM | 0.88 | 1.4 | 1.8 | 1.3 |
| DILTIAZEM 360 PM | 1.4 | 1.7 | 1.9 | 1.3 |
| DILTIAZEM 420 PM | 1.4 | 1.8 | 1.5 | 1.2 |

TABLE 3

Evaluation of Time to Onset of Angina (Seconds) and Time to Onset of
Myocardial Ischemia (Seconds)

| Variable | 6 PM to 8 PM | | | | | 7 AM to 11 AM | | | | |
| --- | --- | --- | --- | --- | --- | --- | --- | --- | --- | --- |
|  | Placebo | 180 PM | 360 PM | 360 AM | 420 PM | Placebo | 180 PM | 360 PM | 360 AM | 420 PM |
| ONSET ANGINA | | | | | | | | | | |
| Dunnett's | | | | | | | | | | |
| N |  | 49 | 46 |  | 39 | 53 | 44 | 37 | 45 | 25 |
| Median | 52 | 59.5 | 41.8 |  | 41.0 | 20.0 | 52.5 | 60.0 | 41.0 | 59.0 |
| Change | 18.8 | 40.7 | 23.0 |  | 22.2 |  | 32.5 | 40.0 | 21.0 | 39.9 |
| Improvement p-value |  | 0.0029 | 0.0109 |  | 0.0114 |  | 0.0021 | 0.0088 | 0.2333 | 0.0240 |
| Kaplan-Meier |  | 21.0 | 22.0 |  | 30.4 | 10.2 | 29.0 | 37.3 | 25.8 | 53.6 |
| % Censored | 11.9 | 361 | 350 |  | 417 | 300 | 390 | 399 | 359 | 460 |
| Median Time | 279 | 82 | 71.0 |  | 138 |  | 90 | 99 | 59 | 160 |
| Improvement p-value |  | 0.0245 | 0.0949 |  | 0.0069 |  | 0.0004 | 0.0006 | 0.0143 | <0.0001 |
| ONSET MYOCARDIAL ISCHEMIA | | | | | | | | | | |
| Dunnett's | | | | | | | | | | |
| N | 52 | 52 | 46 |  | 47 | 45 | 44 | 34 | 47 | 37 |
| Median | 10.0 | 30.0 | 40.3 |  | 35.0 | 20.0 | 55.0 | 78.5 | 47.0 | 59.0 |
| Change |  | 20.0 | 30.3 |  | 25.0 |  | 35.0 | 58.5 | 27.0 | 39.0 |
| Improvement p-value |  | 0.5306 | 0.0230 |  | 0.1018 |  | 0.0203 | 0.0016 | 0.0488 | 0.0247 |
| Kaplan-Meier | 11.9 | 16.1 | 22.0 |  | 16.1 | 23.7 | 29.0 | 40.7 | 22.6 | 33.9 |
| % Censored | 300 | 300 | 299 |  | 344 | 339 | 380 | 387 | 360 | 416 |
| Median Time |  | 0 | −1 |  | 44 |  | 41 | 48.0 | 21.0 | 77.0 |
| Improvement p-value |  | 0.3419 | 0.1222 |  | 0.1667 |  | 0.0348 | 0.0247 | 0.5281 | 0.0094 |

Key findings from these analyses are as follows: p0 1. In general, Diltiazem 360 mg PM and Diltiazem 360 mg AM exhibited similar efficacy with regards to time to onset of angina and time to onset of myocardial ischemia at trough.

2. All nighttime doses of Diltiazem were statistically significantly superior to placebo in reducing the time to onset of angina at trough (6 PM to 8 PM) and at peak (7 AM to 11 AM). Greater efficacy was observed between 7 AM to 11 AM than between 6 PM to 8 PM. Diltiazem 420 mg PM was particularly effective between 7 AM to 11 AM as evidenced by more than 50% of patients randomized to this treatment group never experiencing angina during the TMST. This is an important observation since angina displays a circadian rhythm with the highest incidence occurring between 8 AM to 10 AM.

3. All nighttime doses of Diltiazem were statistically significantly superior to placebo in increasing the time to the onset of myocardial ischemia between 7 AM to 11 AM. At trough, only Diltiazem 360 mg PM and Diltiazem 360 mg AM were statistically significantly superior to placebo and their responses were comparable. For nighttime dosing, greater efficacy was observed during 7 AM to 11 AM than during 6 PM to 8 PM.

In light of the increased risk of angina attacks and myocardial ischemia as well as increased risk of myocardial infarction and sudden death during the morning hours, a comparison of the efficacy of Diltiazem 360 mg PM vs. Diltiazem 360 mg AM during the morning time interval (7 AM to 11 AM) was made for all efficacy variables. As shown in Table 5, nighttime dosing resulted in superior efficacy. About a 4-fold improvement for the primary efficacy variable and about a 2-fold improvement for the secondary variables in favor Diltiazem 360 mg PM was observed.

FIG. 13 provides an overview of adverse events. Treatment emergent adverse events (TEAE) were dose related but comparable to placebo at the highest dose (48% of patients on placebo vs. 55% of patients on Diltiazem 420 mg PM). Less patients on Diltiazem 360 mg AM experienced a TEAE than on Diltiazem 360 mg PM (36% vs. 46%, respectively). However, with regards to TEAE's that the investigator considered treatment related, Diltiazem 360 mg AM and Diltiazem 360 mg PM were comparable (21% vs. 23%, respectively). All adverse events were mild to moderate in nature.

TABLE 5

Comparison of Efficacy of Diltiazem 360 mg PM and Diltiazem 360 mg AM
7 AM to 11 AM

| Variable | Median Change from Baseline | | | Median Improvement v. Placebo | | |
|---|---|---|---|---|---|---|
| | Placebo | 360 PM | 360 AM | 360 PM | 360 AM | PM/AM |
| Total Duration of Exercise | 12.0 | 41.0 | 19.5 | 29.0 | 7.5 | 3.9 |
| Time to Onset Angina | 20.0 | | 41.0 | 40.0 | 21.0 | 1.9 |
| Dunnett Kaplan-Meier | 300 | 60.0 399 | 359 | 99 | 59 | 1.7 |
| Time to Onset Myocardial Ischemia | 20 | | 47.0 | 58.5 | 27.0 | 2.2 |
| Dunnett Kaplan-Meier | 339 | 78.5 387 | 360 | 48 | 21 | 2.3 |

In summary, Diltiazem administered at bedtime demonstrated a flat dose response in median change from baseline to endpoint in total duration of exercise at trough (6 PM to 8 PM) as measured by treadmill stress test (TMST).

All nighttime doses (180 mg, 360 mg, 420 mg) were significantly different from placebo with the 360 mg dose somewhat better than either 180 mg or 420 mg. In contrast, Diltiazem 360 mg administered in the morning was borderline not significantly different from placebo in median change from baseline to endpoint in total duration of exercise at its trough (7 AM to 11 AM). At trough, the 360 mg nighttime dose resulted in about a 2-fold greater improvement in TMST results compared to the 360 mg morning dose.

Between 7 AM and 11 AM (the time period when cardiovascular events are most frequent and the incidence of angina and myocardial ischemia are the greatest), all nighttime doses were significantly different from placebo in change from baseline to endpoint in total duration of exercise as measured by TMST. The dose response was also flat with the 420 mg dose somewhat better than either the 180 mg or 360 mg doses. Greater efficacy was observed between 7 AM and 11 AM coinciding with peak concentrations of Diltiazem than between 6 PM and 8 PM coinciding with trough concentrations of diltiazem. A post-hoc analysis of Diltiazem 360 mg AM at the time corresponding to its peak diltiazem concentration (6 PM to 8 PM) demonstrated a statistically significant difference from placebo in median change from baseline to endpoint in total duration of exercise. The response of Diltiazem 360 mg AM at its peak was comparable to that for Diltiazem 360 mg PM at its peak.

Diltiazem administered at bedtime and in the morning were effective in increasing the time to onset of angina and time to onset of myocardial ischemia at trough. The 420 mg dose was particularly effective in increasing the time to onset of angina during the 7 AM to 11 AM time period. More than 50% of patients randomized to this dose did not experience an angina attack during the TMST.

Diltiazem 360 mg PM was more efficacious than Diltiazem 360 mg AM during the 7 AM to 11 AM time period for all efficacy variables evaluated. About a 4-fold improvement in efficacy for the primary variable and about a 2-fold improvement in efficacy for the secondary variables were observed. Adverse events were dose related, but comparable to placebo at the highest dose (48% of patients for placebo, 55% of patients for Diltiazem 420 mg PM). Adverse events were generally mild to moderate in nature.

What is claimed is:

1. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 hours and about 17 hours ($T_{max}$) after administration of the preparation, the preparation being in a sustained-release dosage form in which the form of Diltiazem is adapted to be control released after administration of the preparation over a period of time and being adapted to release the form of Diltiazem (i) into an aqueous medium at the following rates measured using the method of United States Pharmacopoeia No. XXIII at 100 rpm in 900 ml of water:

(a) between about 1% and about 15% after 2 hours;
(b) between about 7% and about 35% after 4 hours;
(c) between about 30% and about 58% after 8 hours;
(d) between about 55% and about 80% after 14 hours; and
(e) and in excess of about 75% after 24 hours;

and/or (ii) into a buffered medium having a pH between about 5.5 and about 6.5, at the following rates measured using the method of United States Pharmacopoeia No. XXIII at 100 rpm in 900 ml of the buffered medium:
(a) between about 1% and about 25% after about 2 hours;
(b) between about 7% and about 45% after about 4 hours;
(c) between about 30% and about 68% after about 8 hours;
(d) in excess of about 75% after about 24 hours.

2. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 hours and about 17 hours ($T_{max}$) after administration, the preparation being in a sustained-release dosage form in which the form of Diltiazem is adapted to be control released after administration of the preparation over a period of time and being adapted to release the form of Diltiazem (i) into an aqueous medium at the following rates measured using the method of United States Pharmacopoeia No. XXIII at 100 rpm in 900 ml of water:
(a) between about 4% and about 8% after 2 hours;
(b) between about 16% and about 21% after 4 hours;
(c) between about 44% and about 52% after 8 hours;
(d) between about 69% and about 76% after 14 hours; and
(e) and in excess of about 85% after 24 hours;
and or (ii) into a buffered medium having a pH of about 5.8 at the following rates measured using the method of United States Pharmacopoeia No. XXIII at 100 rpm in 900 ml of the buffered medium:
(a) between about 4% and about 15% after 2 hours;
(b) between about 16% and about 30% after 4 hours;
(c) between about 44% and about 62% after 8 hours;
(d) in excess of about 80% after 24 hours.

3. The method of claim 1 wherein the $C_{max}$ of Diltiazem in the blood is obtained between about 11-about 13 hours after administration of the preparation.

4. The method of claim 2 wherein the $C_{max}$ of Diltiazem in the blood is obtained between about 11-about 13 hours after administration of the preparation.

5. The method of claim 1, or 2, wherein the preparation is a diffusion controlled preparation.

6. The method of claim 1, or 2, wherein the preparation releases the form of Diltiazem at a rate of less than about 15% of the total amount of active per hour during dissolution.

7. The method of claim 1, or 2, wherein the preparation comprises a plurality of microgranules each microgranule comprising a central core containing the form of diltiazem coated with a microporous membrane and the central core comprises the form of Diltiazem or pharmaceutically acceptable salt thereof associated with a wetting agent.

8. The method of claim 1, or 2, wherein the preparation comprises a plurality of microgranules, each microgranule comprising a central core containing the form of Diltiazem coated with a microporous membrane and the central core comprises the form of Diltiazem or pharmaceutically acceptable salt thereof associated with a wetting agent and wherein the form of Diltiazem is mixed with the wetting agent.

9. The method of claim 1, or 2, wherein the preparation comprises a plurality of microgranules each microgranule comprising a central core containing the form of Diltiazem coated with a microporous membrane and the central core comprises the form of Diltiazem or pharmaceutically acceptable salt thereof associated with a wetting agent and wherein the form of Diltiazem is mixed with the wetting agent wherein the wetting agent assists to maintain the solubility of the form of Diltiazem in each bead, ensuring that the solubility of the form of Diltiazem is unaffected by the pH of the gastrointestinal tract or other adverse conditions which the composition will meet therein.

10. The method of claim 1, or 2, wherein the preparation comprises a plurality of microgranules, each microgranule comprising a central core containing the form of Diltiazem coated with a microporous membrane and the central core comprises the form of Diltiazem or pharmaceutically acceptable salt thereof associated with a wetting agent and wherein the membrane comprises a water-dispersible or water-soluble polymer and a water-, acid- and base-insoluble polymer of a neutral acrylic polymer including a neutral copolymer of acrylic acid ethyl ester and acrylic acid methyl ester which hydrates the preparation.

11. The method of claim 1, or 2, wherein the preparation comprises a plurality of microgranules, each microgranule comprising a central core containing the form of Diltiazem coated with a microporous membrane and the central core comprises the form of Diltiazem or pharmaceutically acceptable salt thereof associated with a wetting agent wherein the preparation comprises a mixture of the form of Diltiazem and/or pharmaceutically acceptable salt with the wetting agent and the membrane comprises a water-dispersible or water-soluble polymer and a water-, acid- and base-insoluble polymer of a neutral acrylic polymer including a neutral copolymer of acrylic acid ethyl ester and acrylic acid methyl ester which hydrates the preparation.

12. The method of claim 1, or 2, wherein the preparation comprises a plurality of microgranules, each microgranule comprising a central core containing the form of Diltiazem coated with a microporous membrane and the central core comprises the form of Diltiazem or pharmaceutically acceptable salt thereof associated with a wetting agent wherein the membrane comprises a neutral copolymer of acrylic acid ethyl ester and acrylic acid methyl ester and hydroxypropylmethylcellulose.

13. The method of claim 1, or 2, wherein the preparation comprises a plurality of microgranules, each microgranule comprising a central core containing the form of Diltiazem coated with a microporous membrane and the central core comprises the form of Diltiazem or pharmaceutically acceptable salt thereof associated with a wetting agent, and wherein the membrane hydrates the core within the membrane which when put in gastrointestinal fluid causes the membrane to swell while fluid penetrates and hydrates the bead, and dissolves the form of diltiazem and wetting agent and benefits from a concentration gradient through the membrane (high concentration inside and low concentration outside).

14. The method of claim 7 wherein the form of Diltiazem is mixed with the wetting agent and the membrane comprises N,N,N-trimethyl-2-[(2-methyl-1-oxo-2-propenyl)oxy]-chloride ethanaminium polymer with ethyl-2-propenoate and methyl-2-methyl- 2-propenoate, an acrylic polymer and plasticizer combined to form the membrane thereby providing a mechanism of release from this membrane which "washes" the form of diltiazem through pores created when the plasticizer incorporated in the membrane, is released in gastrointestinal fluid.

15. The method of claim 1, or 2, wherein the preparation comprises a plurality of microgranules comprising a central core containing the form of diltiazem coated with a microporous membrane and the central core comprises the form of Diltiazem or a pharmaceutically acceptable salt thereof associated with a dissolution agent (other than a wetting agent) to assist in the release of the form of Diltiazem from the preparation.

16. The method of claim 1, or 2, wherein the preparation comprises a plurality of microgranules comprising a central core containing the form of diltiazem coated with a microporous membrane and the central core comprises Diltiazem or a pharmaceutically acceptable salt thereof associated with a dissolution agent (other than a wetting agent) to assist in the release of the form of Diltiazem from the preparation and wherein the dissolution agent is an organic acid selected from the group consisting of adipic acid, ascorbic acid, citric acid, fumaric acid, malic acid, succinic acid, tartaric acid which permits the form of diltiazem to dissolve in gastrointestinal fluids when the microgranules pass into the higher pH regions of the gastrointestinal tract of the intestine at which pH diltiazem is much less soluble.

17. A method of treating myocardial ischemia in a patient in need thereof comprising the administration of said preparation of claim 1 to the patient in the evening for effective treatment of the patient's myocardial ischemia the next morning.

18. A method of treating myocardial ischemia in a patient in need thereof comprising the administration of the preparation of claim 2 to the patient in the evening for effective treatment of the myocardial ischemia the next morning.

19. A method of treating myocardial ischemia in a patient in need thereof comprising the administration of the preparation of claim 3 to the patient in the evening for effective treatment of the patient's myocardial ischemia the next morning.

20. A method of treating myocardial ischemia in a patient in need thereof comprising the administration of the preparation of claim 4 to the patient in the evening for effective treatment of the patient's myocardial ischemia the next morning.

21. A method of treating myocardial ischemia in a patient in need thereof comprising the administration of the preparation of claim 5 to the patient in the evening for effective treatment of the patient's myocardial ischemia the next morning.

22. A method of treating myocardial ischemia in a patient in need thereof comprising the administration of the preparation of claim 6 to the patient in the evening for effective treatment of the patient's myocardial ischemia the next morning.

23. A method of treating myocardial ischemia in a patient in need thereof comprising the administration of the preparation of claim 7 to the patient in the evening for effective treatment of the patient's myocardial ischemia the next morning.

24. A method of treating myocardial ischemia in a patient in need thereof comprising the administration of the preparation of claim 8 to the patient in the evening for effective treatment of the patient's myocardial ischemia the next morning.

25. A method of treating myocardial ischemia in a patient in need thereof comprising the administration of the preparation of claim 9 to the patient in the evening for effective treatment of the patient's myocardial ischemia the next morning.

26. A method of treating myocardial ischemia in a patient in need thereof comprising the administration of the preparation of claim 10 to the patient in the evening for effective treatment of the patient's myocardial ischemia the next morning.

27. A method of treating myocardial ischemia in a patient in need thereof comprising the administration of the preparation of claim 11 to the patient in the evening for effective treatment of the patient's myocardial ischemia the next morning.

28. A method of treating myocardial ischemia in a patient in need thereof comprising the administration of the preparation of claim 12 to the patient in the evening for the effective treatment of the patient's myocardial ischemia the next morning.

29. A method of treating myocardial ischemia in a patient in need thereof comprising the administration of the preparation of claim 13 to the patient in the evening for effective treatment of the patient's myocardial ischemia the next morning.

30. A method of treating myocardial ischemia in a patient in need thereof comprising the administration of the preparation of claim 14 to the patient in the evening for effective treatment of the myocardial ischemia the next morning.

31. A method of treating myocardial ischemia in a patient in need thereof comprising the administration of the preparation of claim 15 to the patient in the evening for effective treatment of the myocardial ischemia the next morning.

32. A method of treating myocardial ischemia in a patient in need thereof comprising the administration of the preparation of claim 16 to the patient in the evening for effective treatment of the myocardial ischemia the next morning.

33. A method of treating myocardial ischemia in a patient in need thereof comprising the administration of the preparation of claim 1 to the patient in the evening for effective treatment of the patient's myocardial ischemia over a twenty-four hour period.

34. A method of treating myocardial ischemia in a patient in need thereof comprising the administration of the preparation of claim 2 to the patient in the evening for effective treatment of the myocardial ischemia over a twenty-four hour period.

35. A method of treating myocardial ischemia in a patient in need thereof comprising the administration of the preparation of claim 3 to the patient in the evening for effective treatment of the patient's myocardial ischemia over a twenty-four hour period.

36. A method of treating myocardial ischemia in a patient in need thereof comprising the administration of the preparation of claim 4 to the patient in the evening for effective treatment of the patient's myocardial ischemia over a twenty-four hour period.

37. A method of treating myocardial ischemia in a patient in need thereof comprising the administration of the preparation of claim 5 to the patient in the evening for effective treatment of the patient's myocardial ischemia over a twenty-four hour period.

38. A method of treating myocardial ischemia in a patient in need thereof comprising the administration of the preparation of claim 6 to the patient in the evening for effective treatment of the patient's myocardial ischemia over a twenty-four hour period.

39. A method of treating myocardial ischemia in a patient in need thereof comprising the administration of the preparation of claim 7 to the patient in the evening for effective treatment of the patient's myocardial ischemia over a twenty-four hour period.

40. A method of treating myocardial ischemia in a patient in need thereof comprising the administration of the preparation of claim 10 to the patient in the evening for effective treatment of the patient's myocardial ischemia over a twenty-four hour period.

41. A method of treating myocardial ischemia in a patient in need thereof comprising the administration of the preparation of claim 9 to the patient in the evening for effective treatment of the patient's myocardial ischemia over a twenty-four hour period.

42. A method of treating myocardial ischemia in a patient in need thereof comprising the administration of the preparation of claim 10 to the patient in the evening for effective treatment of the patient's myocardial ischemia over a twenty-four hour period.

43. A method of treating myocardial ischemia in a patient in need thereof comprising the administration of the preparation of claim 11 to the patient in the evening for effective treatment of the patient's myocardial ischemia over a twenty-four hour period.

44. A method of treating myocardial ischemia in a patient in need thereof comprising the administration of the preparation of claim 12 to the patient in the evening for the effective treatment of the patient's myocardial ischemia over a twenty-four hour period.

45. A method of treating myocardial ischemia in a patient in need thereof comprising the administration of the preparation of claim 13 to the patient in the evening for effective treatment of the patient's myocardial ischemia over a twenty-four hour period.

46. A method of treating myocardial ischemia in a patient in need thereof comprising the administration of the preparation of claim 14 to the patient in the evening for effective treatment of the myocardial ischemia over a twenty-four hour period.

47. A method of treating myocardial ischemia in a patient in need thereof comprising the administration of the preparation of claim 15 to the patient in the evening for effective treatment of the myocardial ischemia over a twenty-four hour period.

48. A method of treating myocardial ischemia in a patient in need thereof comprising the administration of the preparation of claim 16 to the patient in the evening for effective treatment of the myocardial ischemia over a twenty-four hour period.

49. The method of claim 1, or 2, wherein the preparation contains 180 mg of Diltiazem.

50. The method of claim 1, or 2, wherein the preparation contains 360 mg of Diltiazem.

51. The method of claim 1, or 2, wherein the preparation contains 420 mg of Diltiazem.

52. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation, for providing a $C_{max}$ of Diltiazem in the blood at between about 10 hours and about 17 hours ($T_{max}$) after administration of the preparation, the preparation being in a sustained-release dosage form in which the form of Diltiazem is adapted to be control released after administration of the preparation over a period of time and being adapted to release the Diltiazem.

(i) into an aqueous medium at the following rates measured using the method of United States Pharmacopoeia No. XXIII at 100 rpm in 900 ml of water:

(a) between about 1% and about 15% after 2 hours;
(b) between about 7% and about 35% after 4 hours;
(c) between about 30% and about 58% after 8 hours;
(d) between about 55% and about 80% after 14 hours; and
(e) and in excess of about 75% after 24 hours;

and/or (ii) into a buffered medium having a pH between about 5.5 and about 6.5, at the following rates measured using the method of United States Pharmacopoeia No. XXIII at 100 rpm in 900 ml of the buffered medium:

(a) between about 1% and about 25% after about 2 hours;
(b) between about 7% and about 45% after about 4 hours;
(c) between about 30% and about 68% after about 8 hours;
(d) in excess of about 75% after about 24 hours wherein the preparation comprises a plurality of microgranules, wherein each microgranule comprises a central core of the form of diltiazem or a pharmaceutically acceptable salt thereof, associated with a wetting agent, wherein the central core is coated with a microporous membrane and wherein the wetting agent is selected from the group consisting of:

sugars;
saccharose, mannitol, sorbitol;
lecithins;
$C_{12}$ to $C_{20}$ fatty acid esters of saccarose;
xylose esters or xylites;
polyoxyethylenic glycerrides;
esters of fatty acids and polyoxyethylene;
sorbitan fatty acid esters;
polyglycides-glycerides and polyglycides-alcohols esters and
Metal salts.

53. The method of claim 7 wherein the wetting agent is in association with the diltiazem in the microgranule and not mixed therewith, the membrane comprises a water-soluble or water dispersible polymer or copolymer and a water-, acid- and base-insoluble polymer which is a neutral copolymer of acrylic acid ethyl ester and acrylic acid methyl ester enabling the bead to be hydrated by the introduction of intestinal fluids into the core hydrating the core and therefore mixing the diltiazem and the wetting agent.

54. A method of treating myocardial ischemia in a patient in need thereof comprising the administration of the preparation of claim 52 to the patient in the evening for effective treatment of the patient's myocardial ischemia the next morning.

55. A method of treating myocardial ischemia in a patient in need thereof comprising the administration of the preparation of claim 3 to the patient in the evening for effective treatment of the patient's myocardial ischemia the next morning wherein each microgranule comprises a central core of the form of diltiazem or a pharmaceutically acceptable salt thereof; associated with a wetting agent, wherein the central core is coated with a microporous membrane and wherein the wetting agent is in association with the diltiazem in the microgranule and not mixed therewith, the membrane comprises a water-soluble or water dispersible polymer or copolymer and a water-, acid- and base-insoluble polymer which is a neutral copolymer of acrylic acid ethyl ester and acrylic acid methyl ester enabling the bead to be hydrated by the introduction of intestinal fluids into the core hydrating the core and therefore mixing the diltiazem and the wetting agent.

56. A method of treating myocardial ischemia in a patient in need thereof comprising the administration of the preparation of claim 3 to the patient in the evening for effective treatment of the patient's myocardial ischemia over a twenty-four hour period wherein each microgranule comprises a central core of the form of diltiazem or a pharmaceutically acceptable salt thereof, associated with a wetting agent, wherein the central core is coated with a microporous membrane and wherein the wetting agent is in association with the diltiazem in the microgranule and not mixed therewith, the membrane comprises a water-soluble or water dispersible polymer or copolymer and a water-, acid- and base-insoluble polymer which is a neutral copolymer of acrylic acid ethyl ester and acrylic acid methyl ester enabling the bead to be hydrated by the introduction of intestinal fluids into the core hydrating the core and therefore mixing the diltiazem and the wetting agent.

57. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 hours and about 17 hours ($T_{max}$) after administration of the preparation, the preparation being in a sustained-release dosage form in which the Diltiazem is adapted to be control released after administration of the preparation over a period of time and being adapted to release the Diltiazem (i) into an aqueous medium at the following rates measured using the method of United States Pharmacopoeia No. XXIII at 100 rpm in 900 ml of water:
   (a) between about 1% and about 15% after 2 hours;
   (b) between about 7% and about 35% after 4 hours;
   (c) between about 30% and about 58% after 8 hours;
   (d) between about 55% and about 80% after 14 hours; and
   (e) and in excess of about 75% after 24 hours;
and/or (ii) into a buffered medium having a pH between about 5.5 and about 6.5, at the following rates measured using the method of United States Pharmacopoeia No. XXIII at 100 rpm in 900 ml of the buffered medium:
   (a) between about 1% and about 25% after about 2 hours;
   (b) between about 7% and about 45% after about 4 hours;
   (c) between about 30% and about 68% after about 8 hours;
   (d) in excess of about 75% after about 24 hours, wherein the preparation comprises a plurality of microgranules, wherein each microgranule comprises a central core of the form of diltiazem or a pharmaceutically acceptable salt thereof, associated with a wetting agent, wherein the central core is coated with a microporous membrane in which the core and membrane comprise:

|  | % W/W |
|---|---|
| (a) Diltiazem hydrochloride | 69-73 |
| (b) Microcrystalline cellulose | 8-9.5 |
| (c) Povidone K30 | 1-2 |
| (d) Sucrose stearate | 7-8 |
| (e) Magnesium stearate NF | 0.5-2.5 |
| (f) Talc USP | 0.5-5.0 |
| (g) Titanium dioxide (USP) | 0.15-0.3 |
| (h) Hydroxypropylmethylcellulose 2910 | 0.3-0.6 |
| (i) Polysorbate 80 (tween) | 0.01-0.025 |
| (j) Simeticone C emulsion USP (dry of 30%) | 0.01-0.015 |
| (k) a neutral copolymer of acrylic acid ethyl ester and acrylic acid methyl ester (dry of 30%) | 7-11 |
| Purified water USP | 0 (used for mixing). |

58. A method of treating myocardial ischemia in a patient in need thereof comprising the administration of the preparation of claim 57 to the patient in the evening for effective treatment of the patient's myocardial ischemia the next morning.

59. A method of treating myocardial ischemia in a patient in need thereof comprising the administration of the preparation of claim 57 to the patient in the evening for effective treatment of the patient's myocardial ischemia over a twenty-four hour period.

60. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing about 180 mg to about 420 mg of the form of Diltiazem with excipients to provide controlled (sustained) release of the form of Diltiazem from the preparation for providing a $C_{max}$ of Diltiazem in the blood at between about 10 hours and about 17 hours ($T_{max}$) after administration of the preparation, the preparation being in a sustained-release dosage form in which the Diltiazem is adapted to be control released after administration of the preparation over a period of time and being adapted to release the Diltiazem (i) into an aqueous medium at the following rates measured using the method of United States Pharmacopoeia No. XXIII at 100 rpm in 900 ml of water:
   (a) between about 1% and about 15% after 2 hours;
   (b) between about 7% and about 35% after 4 hours;
   (c) between about 30% and about 58% after 8 hours;
   (d) between about 55% and about 80% after 14 hours; and
   (e) and in excess of about 75% after 24 hours;
and/or (ii) into a buffered medium having a pH between about 5.5 and about 6.5, at the following rates measured using the method of United States Pharmacopoeia No. XXIII at 100 rpm in 900 ml of the buffered medium:
   (a) between about 1% and about 25% after about 2 hours;
   (b) between about 7% and about 45% after about 4 hours;
   (c) between about 30% and about 68% after about 8 hours;
   (d) in excess of about 75% after about 24 hours, wherein the preparation comprises a plurality of microgranules, wherein each microgranule comprises a central core of the form of diltiazem or a pharmaceutically acceptable salt thereof, associated with a wetting agent, wherein the central core is coated with a microporous membrane in which the core and membrane comprise:
   (i) in the core,
      (a) between about 50% and about 85% (% w/w of the total preparation) of Diltiazem or pharmaceutically acceptable salt thereof; and
      (b) between about 2% and about 25% wetting agent (% w/w of the total preparation);
   together with adjuvants; and
   (ii) in the membrane,
      (c) between about 0.1% and about 2% of the total preparation of water-soluble and/or water-dispersible polymer; and
      (d) between about 5% and about 20% (% w/w of the preparation) of a neutral copolymer of acrylic acid ethyl ester and acrylic acid methyl ester, together with adjuvants.

61. A method of treating myocardial ischemia in a patient in need thereof comprising the administration of the preparation of claim 60 to the patient in the evening for effective treatment of the patient's myocardial ischemia the next morning.

62. A method of treating myocardial ischemia in a patient in need thereof comprising the administration of the preparation of claim 60 to the patient in the evening for effective treatment of the patient's myocardial ischemia over a twenty-four hour period.

63. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 and about 17 hours ($T_{max}$) after administration of the preparation, the preparation being in a sustained-release dosage form in which the Diltiazem is adapted to be control released after administration of the preparation over a period of time and being adapted to release the Diltiazem (i) into an aqueous medium at the following rates measured using the method of United States Pharmacopoeia No. XXIII at 100 rpm in 900 ml of water:
  (a) between about 1% and about 15% after 2 hours;
  (b) between about 7% and about 35% after 4 hours;
  (c) between about 30% and about 58% after 8 hours;
  (d) between about 55% and about 80% after 14 hours; and
  (e) and in excess of about 75% after 24 hours;

and/or (ii) into a buffered medium having a pH between about 5.5 and about 6.5, at the following rates measured using the method of United States Pharmacopoeia No. XXIII at 100 rpm in 900 ml of the buffered medium:
  (a) between about 1% and about 25% after about 2 hours;
  (b) between about 7% and about 45% after about 4 hours;
  (c) between about 30% and about 68% after about 8 hours;
  (d) in excess of about 75% after about 24 hours, wherein the preparation comprises a plurality of microgranules, wherein each microgranule comprises a central core of the form of diltiazem or a pharmaceutically acceptable salt thereof, associated with a wetting agent, wherein the central core is coated with a microporous membrane in which the core and membrane comprise:
  (i) in the core,
    (a) between about 69% and about 73% (% w/w of the total preparation) of Diltiazem or pharmaceutically acceptable salt thereof; and
    (b) between about 7% and about 8% wetting agent (% w/w of the total preparation);
  together with adjuvants; and
  (ii) in the membrane,
    (c) between about 0.3% and about 0.6% of the total preparation of water-soluble and/or water-dispersible polymer; and
    (d) between about 7% and about 11% (% w/w of the preparation) of a neutral copolymer of acrylic acid ethyl ester and acrylic acid methyl ester, together with adjuvants.

64. A method of treating myocardial ischemia in a patient in need thereof comprising the administration of the preparation of claim 63 to the patient in the evening for effective treatment of the patient's myocardial ischemia the next morning.

65. The method of claims 1, 2 or 52 wherein the preparation is a tablet and the tablet comprises microgranules in association with wax placebo beads which wax placebo beads serve to absorb the shock placed on the microgranules of Diltiazem during the tablet process, together with excipients and adjuvants.

66. A method of treating myocardial ischemia in a patient in need thereof comprising the administration of the preparation of claim 65 to the patient in the evening for effective treatment of the patient's myocardial ischemia the next morning.

67. A method of treating myocardial ischemia in a patient in need thereof comprising the administration of the preparation of claim 65 to the patient in the evening for effective treatment of the patient's myocardial ischemia over a twenty-four hour period.

68. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 hours about 17 hours ($T_{max}$) after administration of the preparation, the preparation being in a sustained-release dosage form in which the Diltiazem is adapted to be control released after administration of the preparation over a period of time wherein the preparation comprises a plurality of microgranules, each microgranule comprising a central core containing the form of diltiazem coated with a microporous membrane and the central core comprises Diltiazem or pharmaceutically acceptable salt thereof associated with a wetting agent in which the core and membrane comprise:
  (i) in the core,
    (a) between about 50% and about 85% (% w/w of the total preparation) of Diltiazem or pharmaceutically acceptable salt thereof; and
    (b) between about 2% and about 25% wetting agent (% w/w of the total preparation);
  together with adjuvants; and
  (ii) in the membrane,
    (c) between about 0.1% and about 2% of the total preparation of water-soluble and/or water-dispersible polymer; and
    (d) between about 5% and about 20% (% w/w of the preparation) of a neutral copolymer of acrylic acid ethyl ester and acrylic acid methyl ester, together with adjuvants.

69. The method of claim 68 wherein the microgranules are in capsule form.

70. The method of claim 68 wherein the microgranules are in tablet form.

71. The method of claim 68 wherein the core and membrane comprise:
  (i) in the core,
    (a) between about 69% and about 73% (% w/w of the total preparation) of Diltiazem or pharmaceutically acceptable salt thereof; and
    (b) between about 7% and about 8% wetting agent (% w/w of the total preparation);
  together with adjuvants; and
  (ii) in the membrane,
    (c) between about 0.3% and about 0.6% of the total preparation of water-soluble and/or water-dispersible polymer; and (d) between about 7% and about 11% (% w/w of the preparation) of a neutral copolymer of acrylic acid ethyl ester and acrylic acid methyl ester, together with adjuvants.

72. A method of treating myocardial ischemia in a patient in need thereof comprising administration of a controlled-release Galenical preparation of pharmaceutically acceptable form of Diltiazem including the pharmaceutically acceptable salts thereof, for evening dosing every 24 hours containing from about 180 mg to about 420 mg of the form of Diltiazem with excipients to provide controlled (sustained) release of the form of Diltiazem from the preparation for providing a $C_{max}$ of Diltiazem in the blood at between about 10 hours and about 17 hours ($T_{max}$) after administration of the preparation, the preparation being in a sustained-release dosage form in which the Diltiazem is adapted to be control released after administration of the preparation over a period of time wherein the preparation comprises a plurality of microgranules, each microgranule comprising a central core containing the form of diltiazem coated with a microporous membrane and the central core comprises Diltiazem or pharmaceutically acceptable salt thereof associated with a wetting agent in which the core and membrane comprise:

(i) in the core,
  (a) between about 50% and about 85% (% w/w of the total preparation) of Diltiazem or harmaceutically acceptable salt thereof; and
  (b) between about 2% and about 25% wetting agent (% w/w of the total preparation);
together with adjuvants; and
(ii) in the membrane,
  (c) between about 0.1% and about 2% of the total preparation of water-soluble and/or water-dispersible polymer; and
  (d) between about 5% and about 20% (% w/w of the preparation) of a neutral copolymer of acrylic acid ethyl ester and acrylic acid methyl ester, together with adjuvants wherein the core and membrane comprise:

|  | % W/W |
|---|---|
| (a) Diltiazem hydrochloride | 69-73 |
| (b) Microcrystalline cellulose (Avicel ph101) | 8-9.5 |
| (c) Povidone K30 | 1-2 |
| (d) Sucrose stearate (crodesta F150) | 7-8 |
| (e) Magnesium stearate NF | 0.5-2.5 |
| (f) Talc USP | 0.5-5.0 |
| (g) Titanium dioxide (USP) | 0.15-0.3 |
| (h) Hydroxypropylmethylcellulose 2910 | 0.3-0.6 |
| (i) Polysorbate 80 (tween) | 0.01-0.025 |
| (j) Simeticone C emulsion USP (dry of 30%) | 0.01-0.015 |
| (k) a neutral copolymer of acrylic acid ethyl ester and acrylic acid methyl ester (dry of 30%) | 7-11 |
| Purified water USP | 0 (used for mixing). |

73. The method of claim 68 wherein the preparation is a tablet and the tablet comprises microgranules in association with wax placebo beads which wax placebo beads serve to absorb the shock placed on the microgranules of Diltiazem during the tablet process, together with excipients and adjuvants.

74. A method of treating myocardial ischemia in a patient in need thereof comprising the administration of the preparation of claim 68 to the patient in the evening for effective treatment of the myocardial ischemia the next morning.

75. The method of claim 1 wherein the method of treating myocardial ischemia in a patient in need thereof reduces the incidences of myocardial ischemia in said patient.

* * * * *